(12) United States Patent
Ishihara et al.

(10) Patent No.: US 10,829,710 B2
(45) Date of Patent: Nov. 10, 2020

(54) SLIPPERINESS-IMPARTING AGENT AND SLIPPERINESS-IMPARTING METHOD

(71) Applicants: NOF CORPORATION, Tokyo (JP); THE UNIVERSITY OF TOKYO, Tokyo (JP)

(72) Inventors: Kazuhiko Ishihara, Tokyo (JP); Tomozumi Noda, Kawasaki (JP); Masaru Matsuda, Kawasaki (JP); Satoshi Yamada, Kawasaki (JP); Nobuyuki Sakamoto, Kawasaki (JP)

(73) Assignees: NOF CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/313,515

(22) PCT Filed: Jun. 28, 2017

(86) PCT No.: PCT/JP2017/023655
§ 371 (c)(1),
(2) Date: Dec. 27, 2018

(87) PCT Pub. No.: WO2018/003822
PCT Pub. Date: Jan. 4, 2018

(65) Prior Publication Data
US 2019/0316054 A1 Oct. 17, 2019

(30) Foreign Application Priority Data
Jun. 29, 2016 (JP) ................................. 2016-129423

(51) Int. Cl.
*C10M 107/48* (2006.01)
*C08F 230/02* (2006.01)

(52) U.S. Cl.
CPC ......... *C10M 107/48* (2013.01); *C08F 230/02* (2013.01); *C10M 2225/025* (2013.01)

(58) Field of Classification Search
CPC ........... C10M 107/48; C10M 2225/025; C08F 230/02
See application file for complete search history.

(56) References Cited

U.S. PATENT DOCUMENTS

| 10,323,132 B2 * | 6/2019 | Ishihara | C09D 143/02 |
| 2013/0231400 A1 * | 9/2013 | Kim | C08F 230/02 |
| | | | 514/772.3 |

FOREIGN PATENT DOCUMENTS

| JP | 2010-059346 A | 3/2010 | |
| JP | 2010-059367 A | 3/2010 | |
| WO | 2016-140259 A9 | 9/2016 | |
| WO | WO-2016140259 A2 * | 9/2016 | ........... A61L 27/14 |

OTHER PUBLICATIONS

Lin et al; Photoreactive Polymers Bearing a Zwitterionic Phosphorylcholine Group for Surface Modification of Biomaterials; ACS Applied Materials & Interfaces; vol. 7; pp. 17489-17498; Published: Jul. 23, 2105. (Year: 2015).*
Konno T. et al., "Photo-immobilization of a phospholipid polymer for surface modification", Biomaterials 26 (2005), pp. 1381-1388.
Extended European Search Report dated Jan. 15, 2020 from European Patent Office in European Application No. 17820176.0.

* cited by examiner

*Primary Examiner* — Michael P Wieczorek
(74) *Attorney, Agent, or Firm* — Sughrue Mion, PLLC

(57) ABSTRACT

Provided is a lubricity-imparting agent that can impart durable lubricity (in particular, lubricity at the time of wetting) to a substrate. It has been found that a lubricity-imparting agent including a copolymer containing a constitutional unit (A) based on 2-methacryloyloxyethyl phosphorylcholine and a constitutional unit (B) based on a photoreactive functional group-containing monomer, or a copolymer containing a constitutional unit (A) based on 2-methacryloyloxyethyl phosphorylcholine, a constitutional unit (B) based on a photoreactive functional group-containing monomer, and a constitutional unit (C) based on a hydrophobic group-containing monomer can impart durable lubricity to a substrate surface through a simple approach called photoirradiation.

14 Claims, No Drawings

SLIPPERINESS-IMPARTING AGENT AND SLIPPERINESS-IMPARTING METHOD

CROSS REFERENCE TO RELATED APPLICATIONS

This Application is a National Stage of International Application No. PCT/JP2017/023655 filed Jun. 28, 2017, claiming priority based on Japanese Patent Application No. 2016-129423 filed Jun. 29, 2016 incorporated herein by reference.

TECHNICAL FIELD

The present invention relates to a lubricity-imparting agent including a copolymer having at least a phosphorylcholine group serving as a hydrophilic functional group and a photoreactive functional group, and a lubricity-imparting method.

BACKGROUND ART

Many plastic products have been sold in a medical field. Examples thereof include a catheter, a contact lens, an intraocular lens, a cannula, and various tubes. Those medical devices are each attached and detached in a state of being in contact with a biological tissue, and hence the lubricity (in particular, lubricity at the time of wetting) of the surface of each of the devices has been a required item.

For example, there is a risk in that a contact lens that does not have lubricity causes a reduction in wearing feeling at the time of its wearing or causes damage to a tissue on the surface of an eyeball, and there is a risk in that a catheter that does not have lubricity involves pain or causes damage to a tissue at the time of its insertion into a human body. Further, a medical device that does not have lubricity imposes a heavy burden not only on a patient but also on medical personnel required to perform delicate work.

A method involving molding a medical device out of a fluorine-based resin (Patent Literature 1), a method involving coating the medical device with a hydrophilic copolymer, or the like has heretofore been used as a technology for imparting lubricity to the medical device. In particular, the method involving coating the medical device with the hydrophilic copolymer is simple, and for example, it has been known that the hydrophilic copolymer of Patent Literature 2 containing a (meth)acrylate and vinyl alcohol, and the hydrophilic copolymer of Patent Literature 3 containing 2-methacryloyloxyethyl phosphorylcholine each impart high lubricity in addition to biocompatibility. However, many hydrophilic copolymers have each involved a problem in terms of durability because the copolymers are weakly bonded to substrate surfaces.

To solve the problem, in Patent Literature 4, there is a description of a method involving fixing a hydrophilic copolymer containing 2-methacryloyloxyethyl phosphorylcholine and various reactive groups on a substrate surface. In the method, however, the hydrophilic copolymer and a functional group on the substrate surface are caused to react with each other by using a condensation agent, such as 1-ethyl-3-(3-dimethylaminopropyl)carbodiimide hydrochloride, and hence a step of removing the condensation agent and the hydrophilic copolymer that are unreacted after the reaction has been required.

In Patent Literature 5, there is a description of a method involving performing the graft polymerization of 2-methacryloyloxyethyl phosphorylcholine to a substrate having a ketone group on its surface to form a copolymer layer. In the method, however, the presence of a ketone group on the surface of the substrate is required. In addition, the removal of unreacted 2-methacryloyloxyethyl phosphorylcholine after the graft polymerization has been required.

In addition, in each of Patent Literature 6 and Patent Literature 7, there is a description of a copolymer of 2-methacryloyloxyethyl phosphorylcholine and a photoreactive group-containing monomer in order that the copolymer may be easily bonded to a substrate surface. However, a photoreactive group-containing monomer that can improve lubricity, the molecular weight of the copolymer, and the like have not been described.

CITATION LIST

Patent Literature

[PTL 1] JP 2014-50549 A
[PTL 2] JP 2003-144541 A
[PTL 3] WO 2002/015911 A1
[PTL 4] JP 2000-226550 A
[PTL 5] WO 2011/021642 A1
[PTL 6] JP 2010-059346 A
[PTL 7] JP 2010-059367 A

SUMMARY OF INVENTION

Technical Problem

An object of the present invention is to provide a lubricity-imparting agent that can impart durable lubricity (in particular, lubricity at the time of wetting) to a substrate.

Solution to Problem

The inventors of the present invention have made extensive investigations in view of the object, and as a result, have found that a lubricity-imparting agent including a copolymer containing a constitutional unit (A) based on 2-methacryloyloxyethyl phosphorylcholine and a constitutional unit (B) based on a photoreactive functional group-containing monomer, or a copolymer containing a constitutional unit (A) based on 2-methacryloyloxyethyl phosphorylcholine, a constitutional unit (B) based on a photoreactive functional group-containing monomer, and a constitutional unit (C) based on a hydrophobic group-containing monomer can impart durable lubricity to a substrate surface through a simple approach called photoirradiation. Thus, the inventors have completed the pre sent invention.

That is, the present invention includes the following.

[1] A lubricity-imparting agent, including 0.01 mass % to 5.0 mass % of a copolymer having a weight-average molecular weight of from 10,000 to 1,000,000, the copolymer containing 60 mol % to 99 mol % of a constitutional unit (A) based on 2-methacryloyloxyethyl phosphorylcholine represented by the following formula (1) and 1 mol % to 40 mol % of a constitutional unit (B) based on a photoreactive functional group-containing monomer represented by any one of the following formulae (2), (3), and (6):

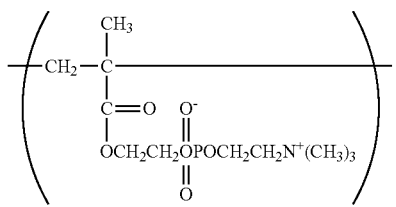
(1)

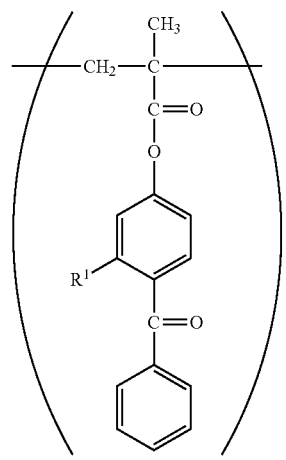
(2)

in the formula (2), $R^1$ represents a hydrogen atom or a hydroxyl group;

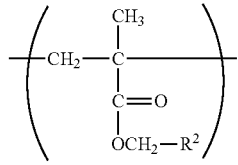
(3)

in the formula (3), $R^2$ represents the following formula (4) or the following formula (5).

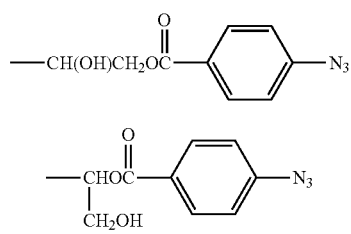
(4)

(5)

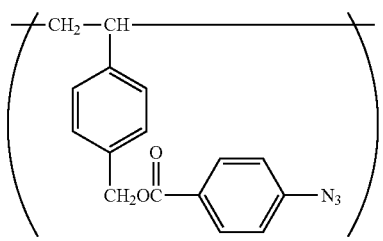
(6)

[2] A lubricity-imparting agent, including 0.01 mass % to 5.0 mass % of a copolymer having a weight-average molecular weight of from 10,000 to 1,000,000, the copolymer containing 60 mol % to 98 mol % of a constitutional unit (A) based on 2-methacryloyloxyethyl phosphorylcholine represented by the following formula (1), 1 mol % to 39 mol % of a constitutional unit (B) based on a photoreactive functional group-containing monomer represented by any one of the following formulae (2), (3), and (6), and 1 mol % to 30 mol % of a constitutional unit (C) based on a hydrophobic group-containing monomer represented by the following formula (7):

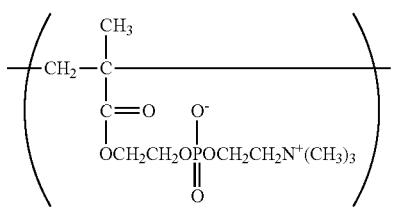
(1)

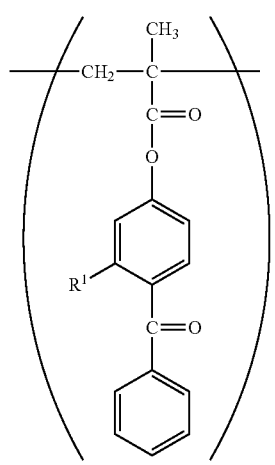
(2)

in the formula (2), $R^1$ represents a hydrogen atom or a hydroxyl group;

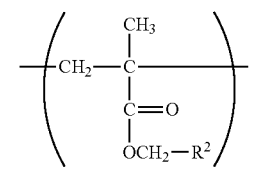
(3)

in the formula (3), $R^2$ represents the following formula (4) or the following formula (5);

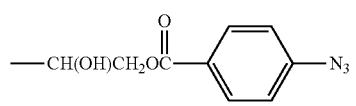
(4)

-continued

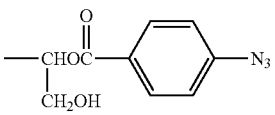
(5)

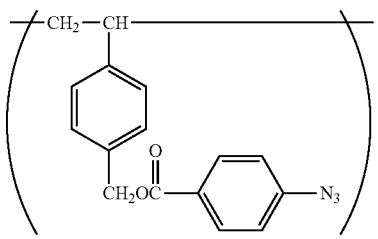
(6)

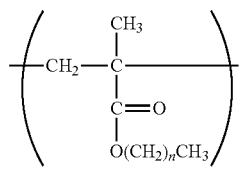
(7)

in the formula (7), n represents from 3 to 17.

[3] A lubricity-imparting agent according to the above-mentioned item [1], wherein the constitutional unit (B) includes a constitutional unit based on 4-methacryloyloxybenzophenone.

[4] A lubricity-imparting agent according to the above-mentioned item [1], wherein the constitutional unit (B) includes a constitutional unit based on 4-methacryloxy-2-hydroxybenzophenone.

[5] A lubricity-imparting agent according to the above-mentioned item [2], wherein the constitutional unit (B) includes a constitutional unit based on 4-methacryloyloxybenzophenone, and the constitutional unit (C) includes a constitutional unit based on butyl methacrylate.

[6] A lubricity-imparting agent according to the above-mentioned item [2], wherein the constitutional unit (B) includes a constitutional unit based on 4-methacryloxy-2-hydroxybenzophenone, and the constitutional unit (C) includes a constitutional unit based on butyl methacrylate.

[7] A lubricity-imparting agent according to the above-mentioned item [2], wherein the constitutional unit (B) includes a constitutional unit based on 4-methacryloyloxybenzophenone, and the constitutional unit (C) includes a constitutional unit based on stearyl methacrylate.

[8] A lubricity-imparting agent according to the above-mentioned item [1], wherein the constitutional unit (B) includes a constitutional unit based on glycidyl methacrylate.

[9] A lubricity-imparting agent according to the above-mentioned item [2], wherein the constitutional unit (B) includes a constitutional unit based on glycidyl methacrylate, and the constitutional unit (C) includes a constitutional unit based on butyl methacrylate.

[10] A lubricity-imparting agent according to the above-mentioned item [2], wherein the constitutional unit (B) includes a constitutional unit based on glycidyl methacrylate, and the constitutional unit (C) includes a constitutional unit based on stearyl methacrylate.

[11] A lubricity-imparting agent according to the above-mentioned item [1], wherein the constitutional unit (B) includes a constitutional unit based on 4-(4-azidobenzoyloxymethyl)styrene.

[12] A lubricity-imparting agent according to the above-mentioned item [2], wherein the constitutional unit (B) includes a constitutional unit based on 4-(4-azidobenzoyloxymethyl)styrene, and the constitutional unit (C) includes a constitutional unit based on butyl methacrylate.

[13] A lubricity-imparting agent according to the above-mentioned item [2], wherein the constitutional unit (B) includes a constitutional unit based on 4-(4-azidobenzoyloxymethyl)styrene, and the constitutional unit (C) includes a constitutional unit based on stearyl methacrylate.

[14] A method of imparting lubricity to a substrate surface, including the following steps (1) and (2):

(1) a step of coating the substrate surface with the lubricity-imparting agent of any one of the above-mentioned items [1] to [13]; and (2) a step of irradiating the substrate surface coated in the step (1) with light to form a crosslinked body on the substrate surface.

[15] A method of forming a crosslinked body, including: coating a substrate surface with the lubricity-imparting agent of any one of the above-mentioned items [1] to [13]; and then irradiating the substrate surface with light to form the crosslinked body on the substrate surface.

[16] A crosslinked body, which is obtained by the method of forming a crosslinked body of the above-mentioned item [15].

[17] A crosslinked body, which is obtained by irradiating the lubricity-imparting agent of any one of the above-mentioned items [1] to [13] with light.

[18] An article, including the crosslinked body of the above-mentioned item [16] or [17].

[19] A lubricity-imparting method, including using a copolymer having a weight-average molecular weight of from 10,000 to 1,000,000, the copolymer containing 60 mol % to 99 mol % of a constitutional unit (A) based on 2-methacryloyloxyethyl phosphorylcholine represented by the following formula (1) and 1 mol % to 40 mol % of a constitutional unit (B) based on a photoreactive functional group-containing monomer represented by any one of the following formulae (2), (3), and (6):

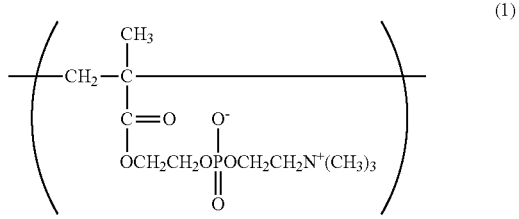
(1)

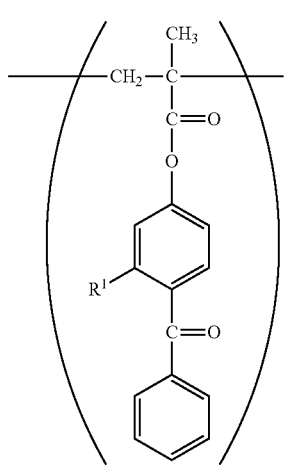

in the formula (2), R¹ represents a hydrogen atom or a hydroxyl group;

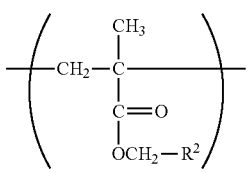

in the formula (3), R² represents the following formula (4) or the following formula (5).

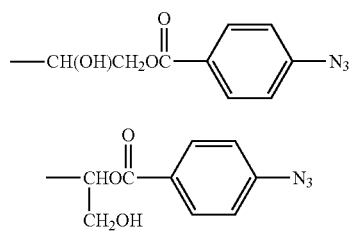

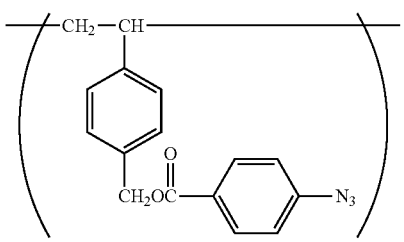

[20] A lubricity-imparting method, including using a copolymer having a weight-average molecular weight of from 10,000 to 1,000,000, the copolymer containing 60 mol % to 98 mol % of a constitutional unit (A) based on 2-methacryloyloxyethyl phosphorylcholine represented by the following formula (1), 1 mol % to 39 mol % of a constitutional unit (B) based on a photoreactive functional group-containing monomer represented by any one of the following formulae (2), (3), and (6), and 1 mol % to 30 mol % of a constitutional unit (C) based on a hydrophobic group-containing monomer represented by the following formula (7):

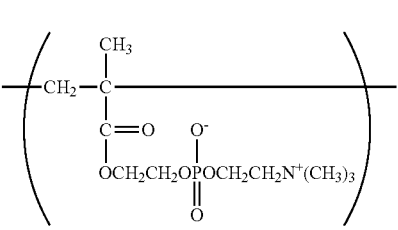

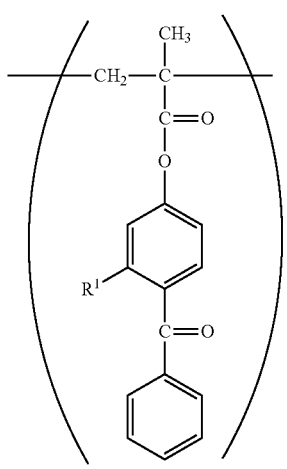

in the formula (2), R¹ represents a hydrogen atom or a hydroxyl group;

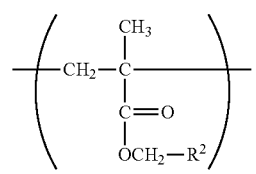

in the formula (3), R² represents the following formula (4) or the following formula (5);

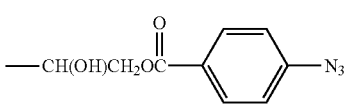

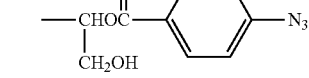

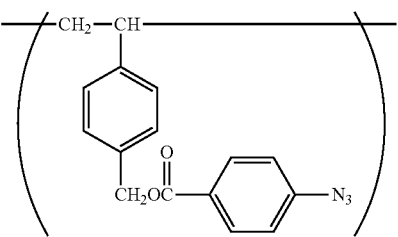

-continued

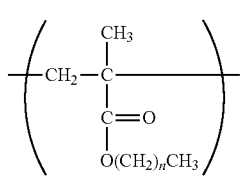

in the formula (7), n represents from 3 to 17.

[21] A lubricity-imparting copolymer having a weight-average molecular weight of from 10,000 to 1,000,000, the copolymer containing 60 mol % to 99 mol % of a constitutional unit (A) based on 2-methacryloyloxyethyl phosphorylcholine represented by the following formula (1) and 1 mol % to 40 mol % of a constitutional unit (B) based on a photoreactive functional group-containing monomer represented by any one of the following formulae (2), (3), and (6):

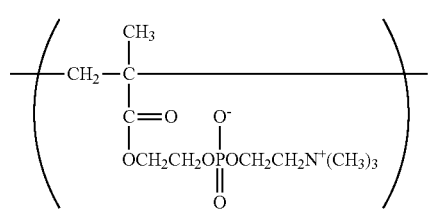

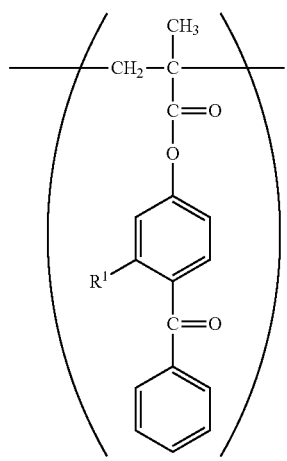

in the formula (2), $R^1$ represents a hydrogen atom or a hydroxyl group;

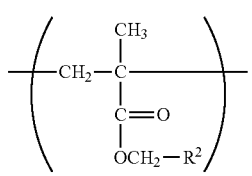

in the formula (3), $R^2$ represents the following formula (4) or the following formula (5).

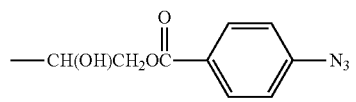

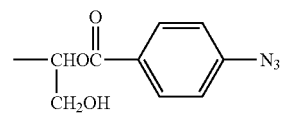

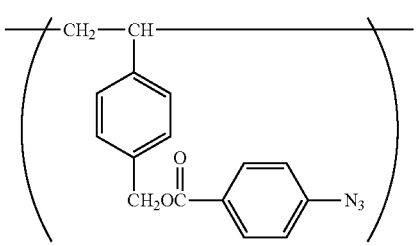

[22] A lubricity-imparting copolymer having a weight-average molecular weight of from 10,000 to 1,000,000, the copolymer containing 60 mol % to 98 mol % of a constitutional unit (A) based on 2-methacryloyloxyethyl phosphorylcholine represented by the following formula (1), 1 mol % to 39 mol % of a constitutional unit (B) based on a photoreactive functional group-containing monomer represented by any one of the following formulae (2), (3), and (6), and 1 mol % to 30 mol % of a constitutional unit (C) based on a hydrophobic group-containing monomer represented by the following formula (7):

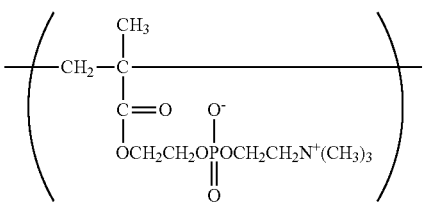

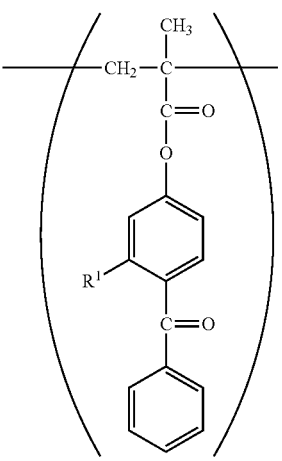

in the formula (2), $R^1$ represents a hydrogen atom or a hydroxyl group;

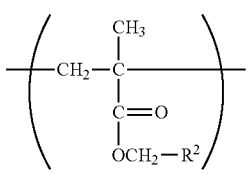 (3)

in the formula (3), $R^2$ represents the following formula (4) or the following formula (5);

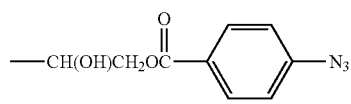 (4)

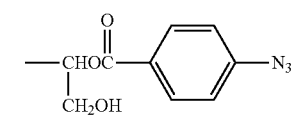 (5)

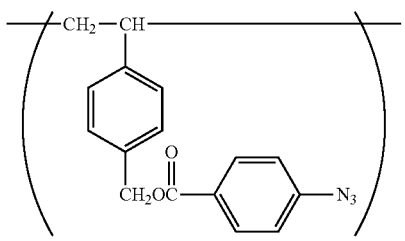 (6)

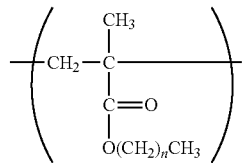 (7)

in the formula (7), n represents from 3 to 17.

[23] A use of a copolymer having a weight-average molecular weight of from 10,000 to 1,000,000, the copolymer containing 60 mol % to 99 mol % of a constitutional unit (A) based on 2-methacryloyloxyethyl phosphorylcholine represented by the following formula (1) and 1 mol % to 40 mol % of a constitutional unit (B) based on a photoreactive functional group-containing monomer represented by any one of the following formulae (2), (3), and (6), in production of a lubricity-imparting agent:

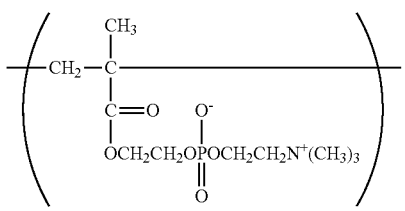 (1)

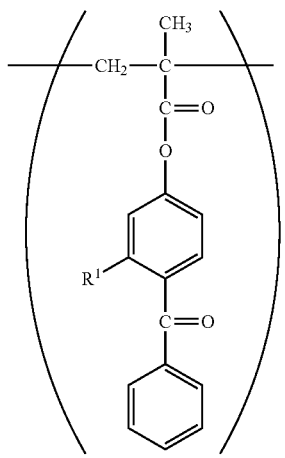 (2)

in the formula (2), $R^1$ represents a hydrogen atom or a hydroxyl group;

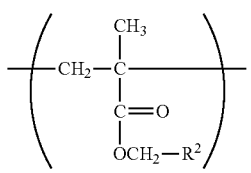 (3)

in the formula (3), $R^2$ represents the following formula (4) or the following formula (5).

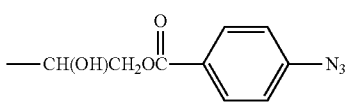 (4)

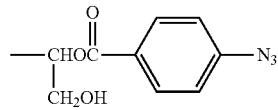 (5)

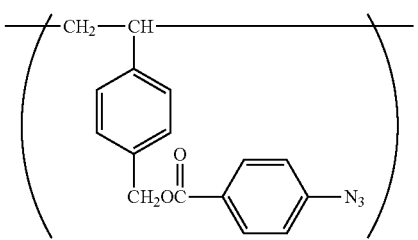 (6)

[24] A use of a copolymer having a weight-average molecular weight of from 10,000 to 1,000,000, the copolymer containing 60 mol % to 98 mol % of a constitutional unit (A) based on 2-methacryloyloxyethyl phosphorylcholine represented by the following formula (1), 1 mol % to 39 mol % of a constitutional unit (B) based on a photoreactive functional group-containing monomer represented by any one of the following formulae (2), (3), and (6), and 1 mol % to 30 mol % of a constitutional unit (C) based on a hydrophobic group-containing monomer represented by the following formula (7), in production of a lubricity-imparting agent:

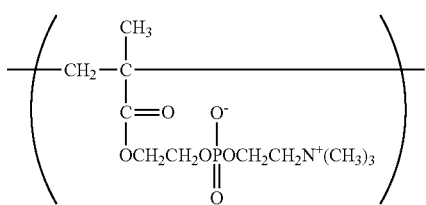
(1)

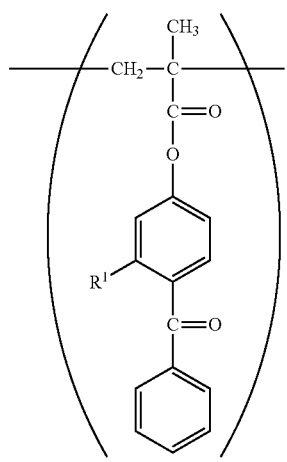
(2)

in the formula (2), R¹ represents a hydrogen atom or a hydroxyl group;

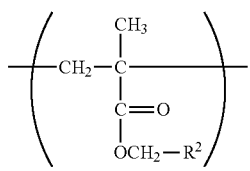
(3)

in the formula (3), R² represents the following formula (4) or the following formula (5);

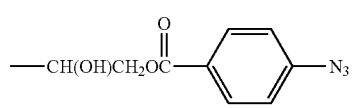
(4)

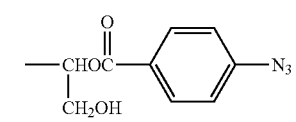
(5)

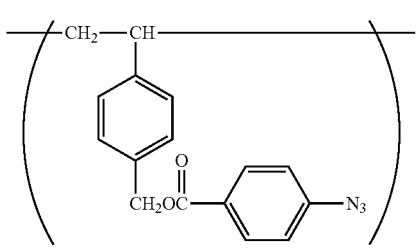
(6)

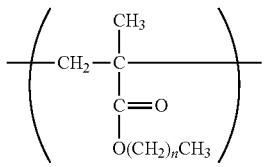
(7)

in the formula (7), n represents from 3 to 17.

Advantageous Effects of Invention

The lubricity-imparting agent of the present invention can impart durable lubricity to a substrate surface. In addition, the article of the present invention has highly durable lubricity.

DESCRIPTION OF EMBODIMENTS

An embodiment of the present invention is described in detail below.

A lubricity-imparting agent of the present invention includes a copolymer containing a constitutional unit (A) based on 2-methacryloyloxyethyl phosphorylcholine and a constitutional unit (B) based on a photoreactive functional group-containing monomer, or a copolymer containing a constitutional unit (A) based on 2-methacryloyloxyethyl phosphorylcholine, a constitutional unit (B) based on a photoreactive functional group-containing monomer, and a constitutional unit (C) based on a hydrophobic group-containing monomer. The constitutional units based on the respective monomers are described below.

[Constitutional Unit (A) Based on 2-Methacryloyloxyethyl Phosphorylcholine]

The copolymer in the lubricity-imparting agent of the present invention contains the constitutional unit (A) based on 2-methacryloyloxyethyl phosphorylcholine represented by the following formula (1). In the constitutional unit (A), a phosphorylcholine group is a polar group having the same structure as that of a phospholipid serving as a main component of a biological membrane. The introduction of the constitutional unit (A) having a phosphorylcholine group into the copolymer can impart not only lubricity but also biocompatibility, such as a protein adsorption-suppressing effect, a cell adsorption-suppressing effect, antithrombogenicity, or hydrophilicity, to the copolymer.

An example of the phosphorylcholine group-containing monomer is 2-(meth)acryloyloxyethyl-2'-(trimethylammonio)ethylphosphate (also known as: 2-methacryloyloxyethyl-2-trimethylammonioethyl phosphate).

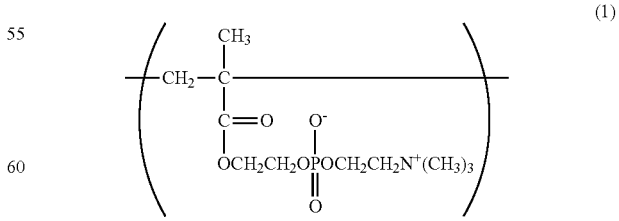
(1)

[Constitutional Unit (B) Based on Photoreactive Functional Group-Containing Monomer]

The copolymer in the lubricity-imparting agent of the present invention contains the constitutional unit (B) based on a photoreactive functional group-containing monomer. A constitutional unit based on a benzophenone group-containing monomer represented by the following formula (2), or a constitutional unit based on an azidophenyl group-containing monomer represented by the following formula (3) or (6) is given as the constitutional unit (B) based on a photoreactive functional group-containing monomer.

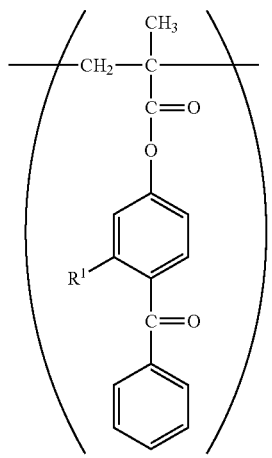
(2)

In the formula (2), $R^1$ represents a hydrogen atom or a hydroxyl group.

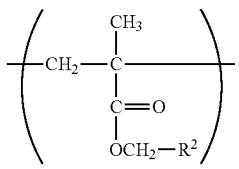
(3)

In the formula (3), $R^2$ represents the following formula (4) or the following formula (5).

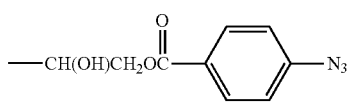
(4)

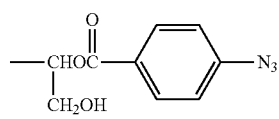
(5)

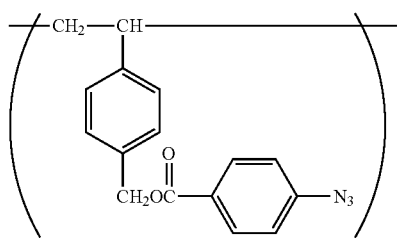
(6)

A benzophenone group is brought into a triplet excited state rich in reactivity by photoirradiation, and can be bonded to a substrate or a copolymer by abstracting a hydrogen atom therefrom. Examples of the benzophenone group-containing monomer include, but not particularly limited to, 4-methacryloyloxybenzophenone (MBP) and 4-methacryloxy-2-hydroxybenzophenone (MHP).

The azidophenyl group produces a nitrene rich in reactivity through photoirradiation, and can be bonded to a substrate or a copolymer by abstracting a hydrogen atom therefrom.

With regard to the constitutional unit based on an azidophenyl group-containing monomer represented by the formula (3), when a copolymer containing glycidyl methacrylate (hereinafter abbreviated as "GMA") represented by the following formula (9) is polymerized, and then 4-azidobenzoic acid (hereinafter abbreviated as "ABA") represented by the following formula (10) is caused to undergo a ring-opening esterification reaction with a glycidyl group of GMA in the presence of triethylamine, a copolymer containing a constitutional unit based on a GMA monomer containing an azidophenyl group (hereinafter abbreviated as "GMA-Az") may be obtained.

The constitutional unit based on an azidophenyl group-containing monomer represented by the formula (6) may be obtained from 4-(4-azidobenzoyloxymethyl)styrene (AzSt) represented by the following formula (8) that may be synthesized by a substitution reaction between chloromethylstyrene (hereinafter abbreviated as "CMS") represented by the following formula (11) and an alkali metal carboxylate represented by the following formula (12). The alkali metal carboxylate is prepared from ABA and an alkali metal salt, and in the formula (12), M represents an alkali metal, such as a lithium atom, a sodium atom, or a potassium atom, preferably a sodium atom or a potassium atom.

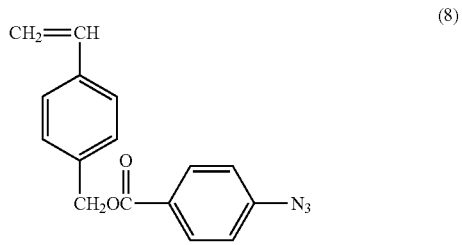
(8)

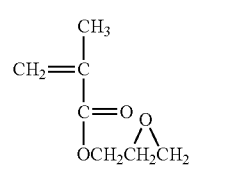
(9)

(10)

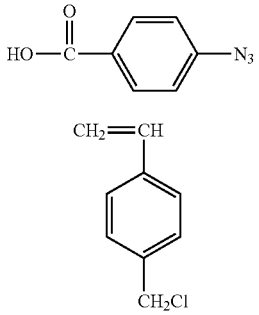
(11)

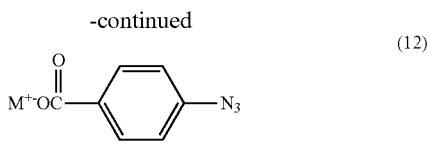

(12)

In the formula (12), M represents an alkali metal.

[Constitutional Unit (C) Based on Hydrophobic Group-Containing Monomer]

The copolymer in the lubricity-imparting agent of the present invention may contain the constitutional unit (C) based on a hydrophobic group-containing monomer represented by the formula (7) in its copolymer structure. A hydrophobic group can improve the applicability of the copolymer through its physical adsorption to a hydrophobic substrate surface.

Examples of the hydrophobic group-containing monomer include, but not particularly limited to, methacrylic acid esters each having a hydrophobic substituent, such as butyl (meth)acrylate, hexyl (meth)acrylate, 2-ethylhexyl (meth)acrylate, decyl (meth)acrylate, dodecyl (meth)acrylate, tridecyl (meth)acrylate, and stearyl (meth)acrylate.

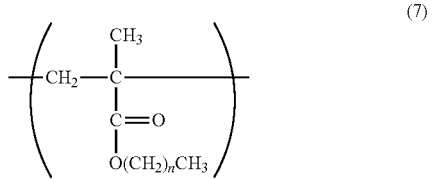

(7)

In the formula (7), n represents from 3 to 17.

[Lubricity-Imparting Agent]

The lubricity-imparting agent of the present invention includes the copolymer containing the constitutional unit (A) based on 2-methacryloyloxyethyl phosphorylcholine and the constitutional unit (B) based on a photoreactive functional group-containing monomer, or the copolymer containing the constitutional unit (A) based on 2-methacryloyloxyethyl phosphorylcholine, the constitutional unit (B) based on a photoreactive functional group-containing monomer, and the constitutional unit (C) based on a hydrophobic group-containing monomer at a concentration of from 0.01 mass % to 5.0 mass %, preferably from 0.01 mass % to 2.5 mass %, more preferably from 0.1 mass % to 1.0 mass %.

The copolymer to be incorporated into the lubricity-imparting agent of the present invention is a copolymer containing 60 mol % to 99 mol % of the constitutional unit (A) based on 2-methacryloyloxyethyl phosphorylcholine and 1 mol % to 40 mol % of the constitutional unit (B) based on a photoreactive functional group-containing monomer, or a copolymer containing 60 mol % to mol % of the constitutional unit (A) based on 2-methacryloyloxyethyl phosphorylcholine, 1 mol % to 39 mol % of the constitutional unit (B) based on a photoreactive functional group-containing monomer, and 1 mol % to 30 mol % of the constitutional unit (C) based on a hydrophobic group-containing monomer.

The weight-average molecular weight of the copolymer to be incorporated into the lubricity-imparting agent of the present invention falls within the range of from 10,000 to 1,000,000, preferably from 15,000 to 750,000, more preferably from 25,000 to 520,000 in terms of the exhibition of satisfactory lubricity.

The lubricity-imparting agent of the present invention is not particularly limited as long as the agent includes the copolymer as an effective component, and the agent may include a solvent for dissolving the copolymer. A lower alcohol, such as ethanol, methanol, normal propanol, or isopropanol, purified water, pure water, ultrapure water, ion-exchanged water, physiological saline, or a buffer, such as a phosphate buffer, a Tris-hydrochloric acid buffer, or a HEPES buffer, or a product obtained by mixing two or more of these solvents at an arbitrary ratio may be used as the solvent for dissolving the copolymer.

The lubricity-imparting agent of the present invention includes 0.01 mass % to 5.0 mass %, preferably 0.01 mass % to 2.5 mass %, more preferably 0.1 mass % to 1.0 mass % of the copolymer. When the content is excessively high, the agent cannot be uniformly applied, and when the content is excessively low, an effective lubricity-improving effect is not obtained.

The lubricity-imparting agent of the present invention may contain, in addition to the copolymer, a lower alcohol, water, a buffer, or the like, and may be further blended with, as required, an antiseptic agent (e.g., sodium benzoate, sodium salicylate, potassium sorbate, or benzalkonium chloride), a surfactant (e.g., polysorbate 80, sorbitan monooleate, squalane, or sodium lauryl sulfate), a hydrophilic copolymer (e.g., polyethylene glycol or polyvinyl alcohol), a humectant (e.g., concentrated glycerin, methyl cellulose, hyaluronic acid, a 2-methacryloyloxyethyl phosphorylcholine polymer, a 2-methacryloyloxyethyl phosphorylcholine-butyl methacrylate copolymer liquid, or liquid paraffin), an amino acid (e.g., L-ascorbic acid, alanine, L-glutamic acid, or L-methionine), a medicinal component (e.g., indomethacin or dexamethasone), a blood anticoagulant (e.g., heparin, sodium citrate, ethylenediaminetetraacetic acid, acetylsalicylic acid, urokinase, or warfarin), an anticancer agent (e.g., taxol, leustatin, adriacin, bleomycin, or imatinib), an antibiotic (e.g., kanamycin, streptomycin, or polymyxin B), an absorption promoter (e.g., sodium caprate), a stabilizing agent (e.g., calcium citrate, natural vitamin E, human serum albumin, or dextran), a radiation absorber (e.g., a metal, such as barium, silver, tin, platinum, gold, or zirconium, and a compound, such as a sulfate, a carbonate, or a nitrate, containing any of those metals), and various compounds other than the above-mentioned compounds.

[Polymerization Reaction of Copolymer]

The polymerization reaction of the copolymer in the lubricity-imparting agent of the present invention may be performed by a known method, such as radical polymerization, such as bulk polymerization, suspension polymerization, emulsion polymerization, or solution polymerization, in the presence of a radical polymerization initiator, such as a peroxide or an azo compound, after the inside of a reaction system has been purged with an inert gas, such as nitrogen, carbon dioxide, argon, or helium, or in the inert gas atmosphere.

The polymerization reaction is preferably the solution polymerization from the viewpoint of, for example, the purification of the polymer to be obtained. Those polymerization reactions provide copolymers having constitutional units represented by the following formulae (13) to (18).

"a", "b", and "c" merely represent the constituent ratios of the constitutional units, and the copolymer may be of any one of the following structures: a random copolymer, a block copolymer, and a graft copolymer, and a combination of two or more thereof.

In each of the copolymers represented by the formulae (13) to (15), "a" and "b" (molar ratios) satisfy relationships of a/(a+b)=0.60 to 0.99 and b/(a+b)=0.01 to 0.40. In each of the copolymers represented by the formulae (16) to (18), "a", "b", and "c" satisfy relationships of a/(a+b+c)=0.60 to 0.98, b/(a+b+c)=0.01 to 0.39, and c/(a+b+c)=0.01 to 0.30.

As another representation, in each of the copolymers represented by the formulae (13) to (15), the ratio "a" of the phosphorylcholine constitutional unit (A) of the copolymer of the present invention and the ratio "b" of the constitutional unit (B) based on a photoreactive functional group-containing monomer thereof satisfy a ratio "a:b" of 100:1 to 67.

In addition, in each of the copolymers represented by the formulae (16) to (18), the ratio "a" of the phosphorylcholine constitutional unit (A) of the copolymer of the present invention, the ratio "b" of the constitutional unit (B) based on a photoreactive functional group-containing monomer thereof, and the ratio "c" of the constitutional unit (C) based on a hydrophobic group-containing monomer thereof satisfy a ratio "a:b:c" of 100:1 to 65:1 to 50.

Further, as can be seen from Examples below, the ratio "a" of the phosphorylcholine constitutional unit (A) of the copolymer of the present invention, the ratio "b" of the constitutional unit (B) based on a photoreactive functional group-containing monomer thereof, and the ratio "c" of the constitutional unit (C) based on a hydrophobic group-containing monomer thereof more preferably satisfy a ratio "a:b:c" of 0.6 to 0.8:0.05 to 0.1:0.1 to 0.3 (Examples 12, 16, 19, 21, and 23).

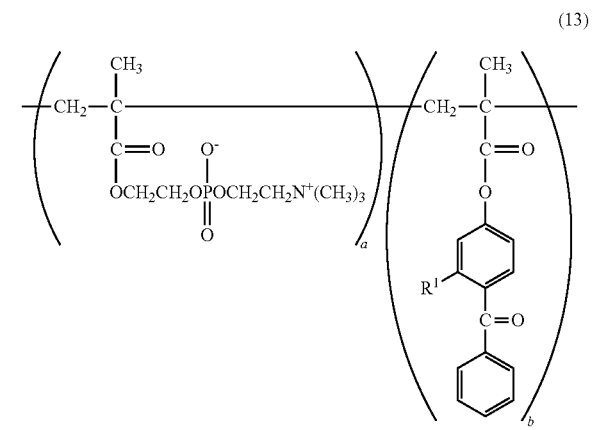

(13)

In the formula (13), $R^1$ represents a hydrogen atom or a hydroxyl group.

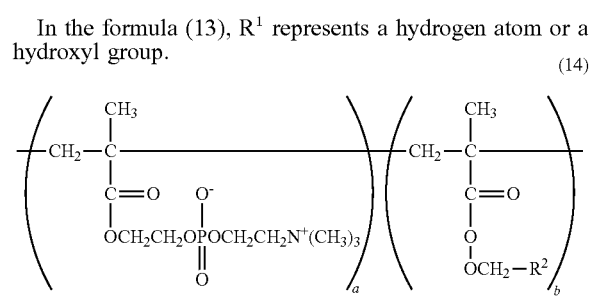

(14)

In the formula (14), $R^2$ represents the following formula (4) or (5).

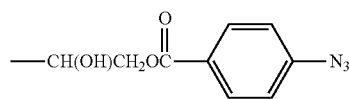

(4)

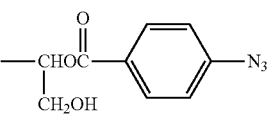

(5)

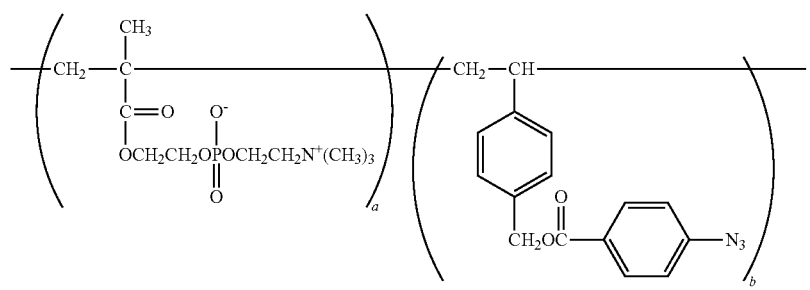

(15)

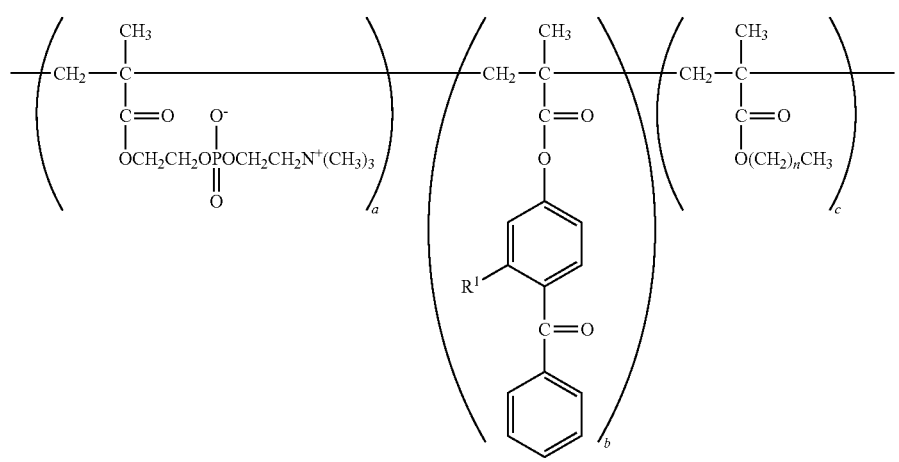

(16)

In the formula (16), $R^1$ represents a hydrogen atom or a hydroxyl group, and n represents from 3 to 17.

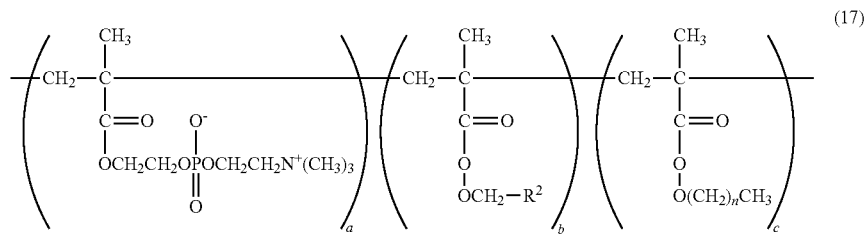

(17)

In the formula (17), $R^2$ represents the formula (4) or (5), and n represents from 3 to 17.

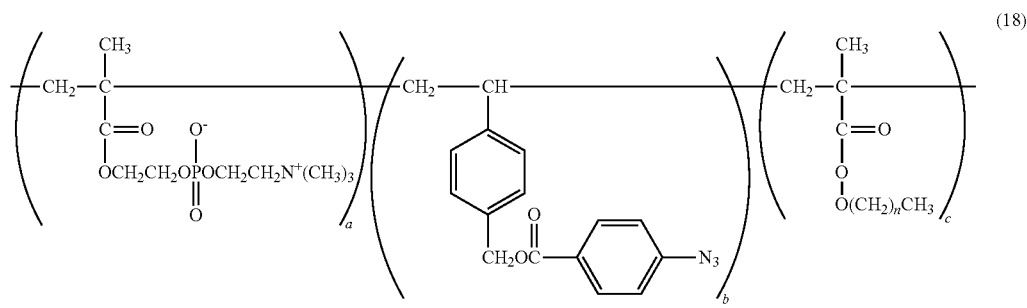

(18)

In the formula (18), n represents from 3 to 17.

A constitutional unit except the constitutional unit (A) based on 2-methacryloyloxyethyl phosphorylcholine, the constitutional unit (B) based on a photoreactive functional group-containing monomer, and the constitutional unit (C) based on a hydrophobic group-containing monomer may be incorporated into the copolymer to the extent that the lubricity-improving action of the lubricity-imparting agent is not adversely affected.

Examples thereof may include constitutional units based on a linear or branched alkyl (meth)acrylate, a cyclic alkyl (meth)acrylate, an aromatic group-containing (meth)acrylate, a styrene-based monomer, a vinyl ether monomer, a vinyl ester monomer, a hydrophilic hydroxyl group-containing (meth)acrylate, an acid group-containing monomer, a nitrogen-containing group-containing monomer, an amino group-containing monomer, and a cationic group-containing monomer.

Examples of the linear or branched alkyl (meth)acrylate include methyl (meth)acrylate, ethyl (meth)acrylate, butyl (meth)acrylate, and 2-ethylhexyl (meth)acrylate.

An example of the cyclic alkyl (meth)acrylate is cyclohexyl (meth)acrylate.

Examples of the aromatic group-containing (meth)acrylate include benzyl (meth)acrylate and phenoxyethyl (meth)acrylate.

Examples of the styrene-based monomer include styrene, methylstyrene, and chloromethylstyrene.

Examples of the vinyl ether monomer include methyl vinyl ether and butyl vinyl ether.

Examples of the vinyl ester monomer include vinyl acetate and vinyl propionate.

Examples of the hydrophilic hydroxyl group-containing (meth)acrylate include polyethylene glycol (meth)acrylate, polypropylene glycol (meth)acrylate, 2-hydroxyethyl (meth)acrylate, 2-hydroxybutyl (meth)acrylate, and 4-hydroxybutyl (meth)acrylate.

Examples of the acid group-containing monomer include (meth)acrylic acid, styrenesulfonic acid, and (meth)acryloyloxyphosphonic acid.

An example of the nitrogen-containing group-containing monomer is N-vinylpyrrolidone.

Examples of the amino group-containing monomer include aminoethyl (meth)acrylate, dimethylamino (meth)acrylate, and N,N-dimethylaminopropyl (meth)acrylamide.

An example of the cationic group-containing monomer is 2-hydroxy-3-(meth)acryloyloxypropyltrimethylammonium chloride.

<Lubricity-Imparting Method>

A lubricity-imparting method including using the lubricity-imparting agent of the present invention is described.

First, the lubricity-imparting agent of the present invention can be used in plastic, metal, and silicone articles (e.g., a guide wire, a stent, an artificial joint, and a silicone tube), in particular, the plastic articles. The plastic articles are, for example, articles formed from polystyrene, polyethylene, polypropylene, polyethylene terephthalate, polyolefin, polyether ether ketone, polyurethane, and polycarbonate, and are particularly preferably, for example, a catheter, a guide wire (whose surface is covered with a plastic), a contact lens, and an intraocular lens. When the surface of any such plastic article is treated with the lubricity-imparting agent of the present invention, the lubricity of the surface can be improved and the lubricity has durability. More specifically, an article in which the lubricity-imparting agent of the present invention is used is preferably an article from which a hydrogen atom can be abstracted, such as a plastic material, but the use of an appropriate binder enables the agent to be used in an article except the plastic articles.

Next, a method of coating the surface of a substrate with the lubricity-imparting agent of the present invention is described. A spin coating method, a spray coating method, a cast coating method, a dip coating method, a roll coating method, a flow coating method, or the like may be used as the method of coating the surface with the lubricity-imparting agent of the present invention, but the dip coating method or the cast coating method is preferred. Further, after the coating, the agent may be dried as required at room temperature or by being warmed.

The substrate coated with (having applied thereto) the lubricity-imparting agent of the present invention is irradiated with light having a wavelength of from 200 nm to 400 nm, preferably light having a wavelength of from 254 nm to 365 nm. Further, an excess lubricity-imparting agent may be washed off by washing the substrate with a proper solvent, such as pure water, ethanol, or methanol, after the photoirradiation.

Lubricity can be imparted to an article (in particular, a plastic article) by such lubricity-imparting method as described above.

<Method of Forming Crosslinked Body, Crosslinked Body, and Article>

A method of forming a crosslinked body of the present invention includes: coating a substrate surface with the lubricity-imparting agent of the present invention; and then irradiating the substrate surface with light to form the crosslinked body on the substrate surface.

A crosslinked body of the present invention may be obtained by the method of forming a crosslinked body of the present invention. Alternatively, the crosslinked body may be obtained by irradiating the lubricity-imparting agent of the present invention with light.

An article of the present invention includes the crosslinked body of the present invention.

The combination of the constitutional unit (A) based on 2-methacryloyloxyethyl phosphorylcholine of the copolymer of the present invention, the constitutional unit (B) based on a photoreactive functional group-containing monomer thereof, and the constitutional unit (C) based on a hydrophobic group-containing monomer thereof is as described below, but is not particularly limited (the left portion represents the constitutional unit (A), the central portion represents the constitutional unit (B), and the right portion represents the constitutional unit (C)).

MPC-MBP
MPC-MBP-butyl methacrylate
MPC-MBP-hexyl methacrylate
MPC-MBP-2-ethylhexyl methacrylate
MPC-MBP-decyl methacrylate
MPC-MBP-dodecyl methacrylate
MPC-MBP-tridecyl methacrylate
MPC-MBP-stearyl methacrylate
MPC-MHP
MPC-MHP-butyl methacrylate
MPC-MHP-hexyl methacrylate
MPC-MHP-2-ethylhexyl methacrylate
MPC-MHP-decyl methacrylate
MPC-MHP-dodecyl methacrylate
MPC-MHP-tridecyl methacrylate
MPC-MHP-stearyl methacrylate
MPC-GMA-Az
MPC-GMA-Az-butyl methacrylate
MPC-GMA-Az-hexyl methacrylate
MPC-GMA-Az-2-ethylhexyl methacrylate
MPC-GMA-Az-decyl methacrylate
MPC-GMA-Az-dodecyl methacrylate
MPC-GMA-Az-tridecyl methacrylate
MPC-GMA-Az-stearyl methacrylate
MPC-Az St
MPC-AzSt-butyl methacrylate
MPC-AzSt-hexyl methacrylate
MPC-AzSt-2-ethylhexyl methacrylate
MPC-AzSt-decyl methacrylate
MPC-AzSt-dodecyl methacrylate
MPC-AzSt-tridecyl methacrylate
MPC-AzSt-stearyl methacrylate Further, as can be seen from Examples below, more preferred combinations of the phosphorylcholine constitutional unit, photoreactive constitutional unit, and hydrophobic constitutional unit of the copolymer of the present invention are MPC-GMA-Az-butyl methacrylate (Example 12), MPC-GMA-Az-stearyl methacrylate (Example 16), MPC-AzSt-butyl methacrylate (Polymerization Example 19 and Polymerization Example 21), and MPC-AzSt-stearyl methacrylate (Polymerization Example 23).

Accordingly, GMA-Az and AzSt are each particularly preferred as the photoreactive constitutional unit of the copolymer of the present invention.

The present invention is also directed to a lubricity-imparting method, including using a copolymer having a weight-average molecular weight of from 10,000 to 1,000,000, the copolymer containing 60 mol % to 99 mol % of a constitutional unit (A) based on 2-methacryloyloxyethyl phosphorylcholine represented by the following formula (1) and 1 mol % to 40 mol % of a constitutional unit (B) based on a photoreactive functional group-containing monomer represented by any one of the following formulae (2), (3), and (6):

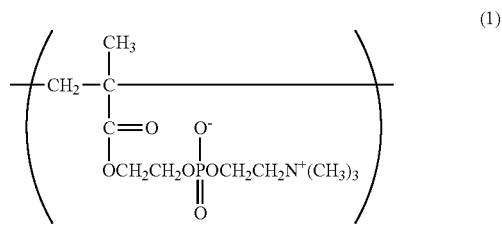

(1)

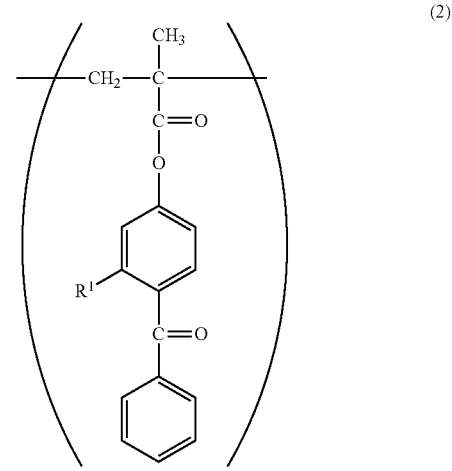

(2)

In the formula (2), R¹ represents a hydrogen atom or a hydroxyl group.

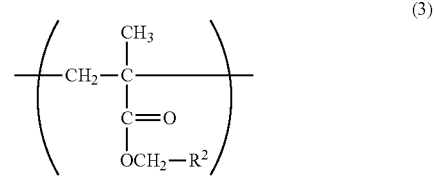

(3)

In the formula (3), $R^2$ represents the following formula (4) or the following formula (5).

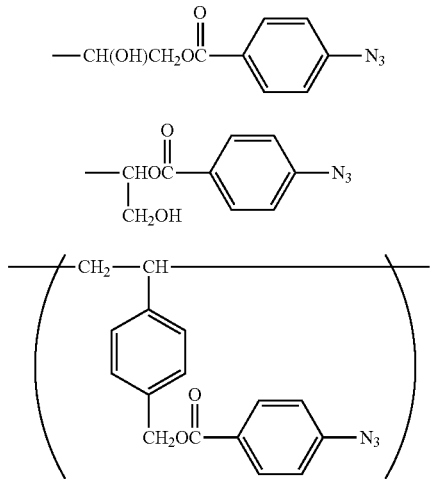

The present invention is also directed to a lubricity-imparting method, including using a copolymer having a weight-average molecular weight of from 10,000 to 1,000,000, the copolymer containing 60 mol % to 98 mol % of a constitutional unit (A) based on 2-methacryloyloxyethyl phosphorylcholine represented by the following formula (1), 1 mol % to 39 mol % of a constitutional unit (B) based on a photoreactive functional group-containing monomer represented by any one of the following formulae (2), (3), and (6), and 1 mol % to 30 mol % of a constitutional unit (C) based on a hydrophobic group-containing monomer represented by the following formula (7):

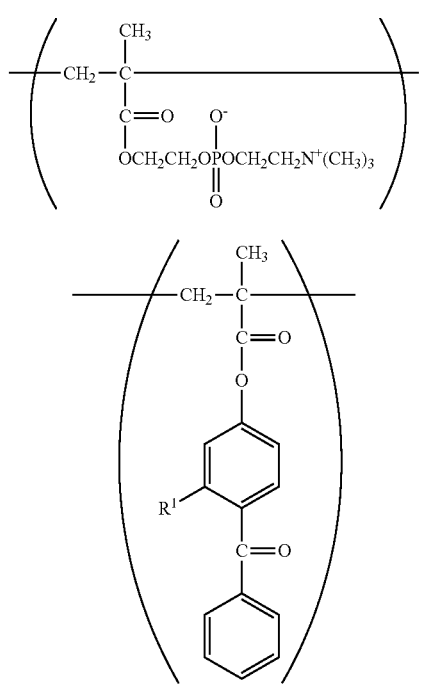

In the formula (2), $R^1$ represents a hydrogen atom or a hydroxyl group.

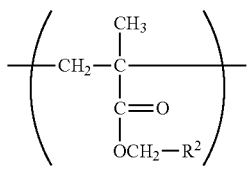

In the formula (3), $R^2$ represents the following formula (4) or the following formula (5).

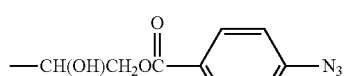

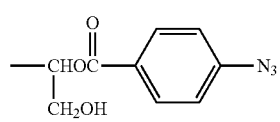

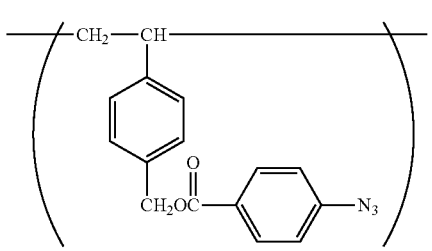

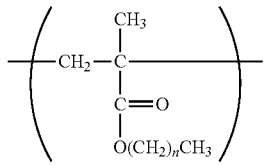

In the formula (7), n represents from 3 to 17.

The present invention is also directed to a lubricity-imparting copolymer having a weight-average molecular weight of from 10,000 to 1,000,000, the copolymer containing 60 mol % to 99 mol % of a constitutional unit (A) based on 2-methacryloyloxyethyl phosphorylcholine represented by the following formula (1) and 1 mol % to 40 mol % of a constitutional unit (B) based on a photoreactive functional group-containing monomer represented by any one of the following formulae (2), (3), and (6):

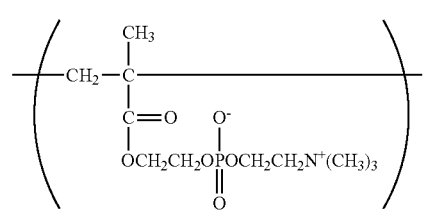

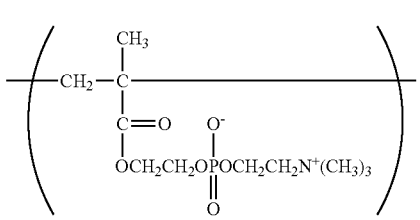

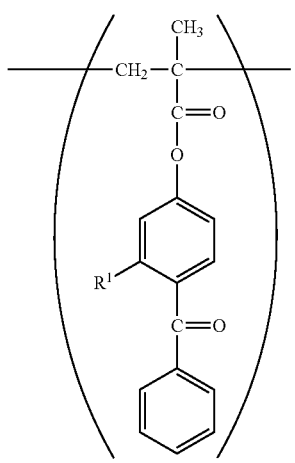

In the formula (2), $R^1$ represents a hydrogen atom or a hydroxyl group.

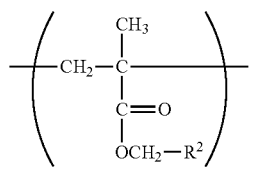

In the formula (3), $R^2$ represents the following formula (4) or the following formula (5).

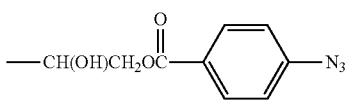

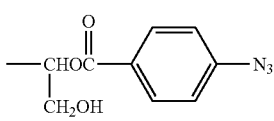

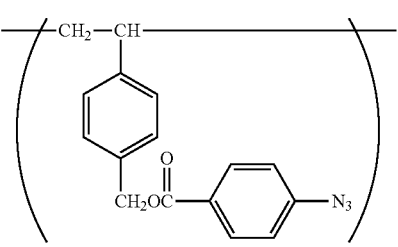

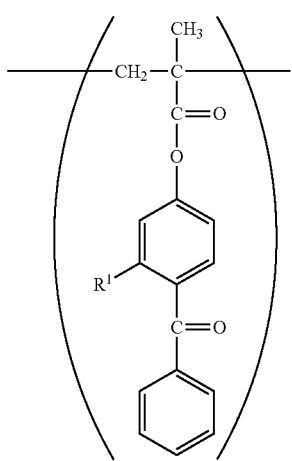

In the formula (2), $R^1$ represents a hydrogen atom or a hydroxyl group.

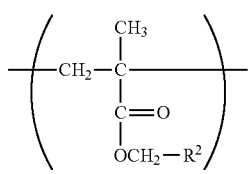

In the formula (3), $R^2$ represents the following formula (4) or the following formula (5).

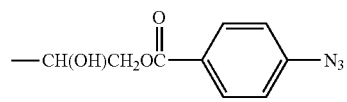

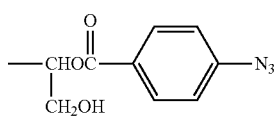

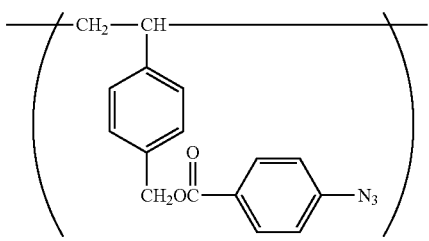

The present invention is also directed to a lubricity-imparting copolymer having a weight-average molecular weight of from 10,000 to 1,000,000, the copolymer containing 60 mol % to 98 mol % of a constitutional unit (A) based on 2-methacryloyloxyethyl phosphorylcholine represented by the following formula (1), 1 mol % to 39 mol % of a constitutional unit (B) based on a photoreactive functional group-containing monomer represented by any one of the following formulae (2), (3), and (6), and 1 mol % to 30 mol % of a constitutional unit (C) based on a hydrophobic group-containing monomer represented by the following formula (7):

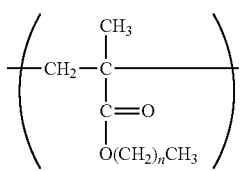

In the formula (7), n represents from 3 to 17.

The present invention is also directed to a use of a copolymer having a weight-average molecular weight of from 10,000 to 1,000,000, the copolymer containing 60 mol % to 99 mol % of a constitutional unit (A) based on 2-methacryloyloxyethyl phosphorylcholine represented by the following formula (1) and 1 mol % to 40 mol % of a constitutional unit (B) based on a photoreactive functional group-containing monomer represented by any one of the following formulae (2), (3), and (6), in production of a lubricity-imparting agent:

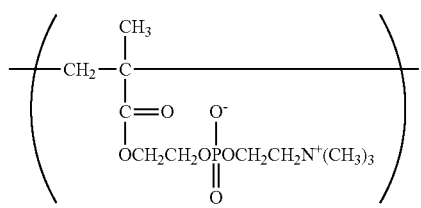

(1)

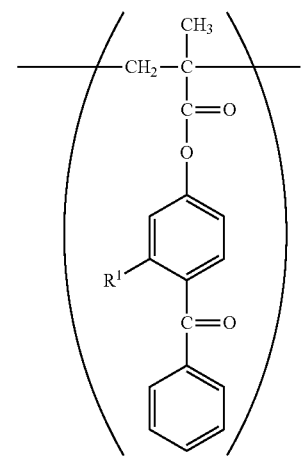

(2)

In the formula (2), $R^1$ represents a hydrogen atom or a hydroxyl group.

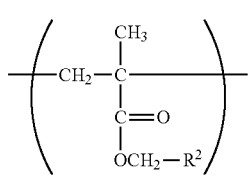

(3)

In the formula (3), $R^2$ represents the following formula (4) or the following formula (5).

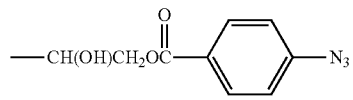

(4)

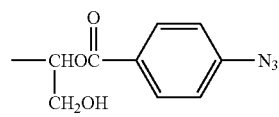

(5)

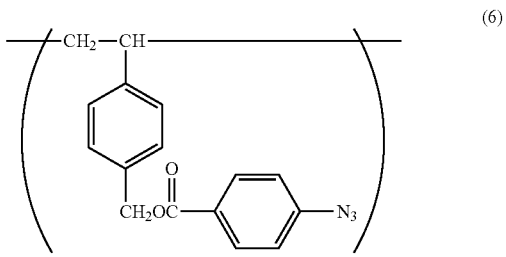

(6)

The present invention is also directed to a use of a copolymer having a weight-average molecular weight of from 10,000 to 1,000,000, the copolymer containing 60 mol % to 98 mol % of a constitutional unit (A) based on 2-methacryloyloxyethyl phosphorylcholine represented by the following formula (1), 1 mol % to 39 mol % of a constitutional unit (B) based on a photoreactive functional group-containing monomer represented by any one of the following formulae (2), (3), and (6), and 1 mol % to 30 mol % of a constitutional unit (C) based on a hydrophobic group-containing monomer represented by the following formula (7), in production of a lubricity-imparting agent:

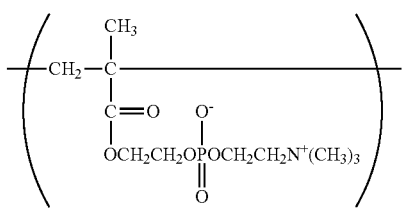

(1)

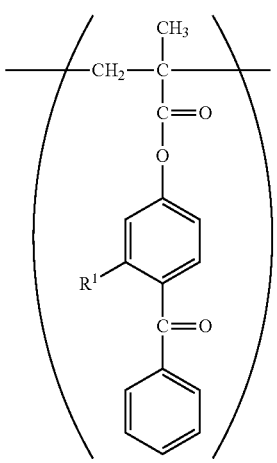

(2)

In the formula (2), $R^1$ represents a hydrogen atom or a hydroxyl group.

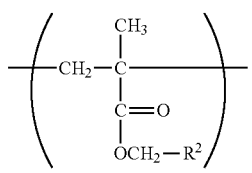

(3)

In the formula (3), R² represents the following formula (4) or the following formula (5).

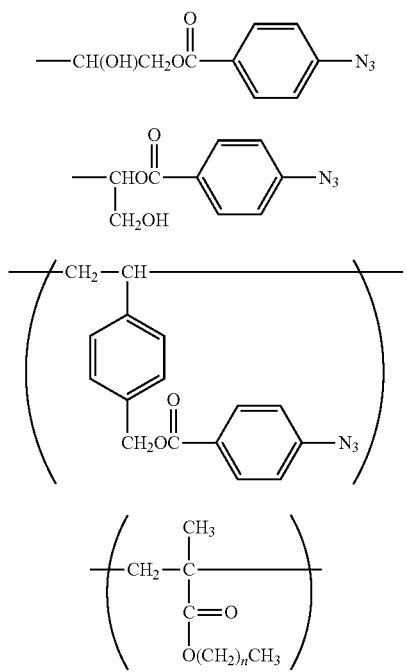

(4)

(5)

(6)

(7)

In the formula (7), n represents from 3 to 17.

EXAMPLES

The present invention is described in more detail below by way of Examples and Comparative Examples.

<Addition of Azidobenzoic Acid to Glycidyl Methacrylate (Addition of ABA to Copolymer)>

Copolymers each containing glycidyl methacrylate (GMA) were polymerized under polymerization conditions shown in Table 1 and Table 2 to be described later. After that, 1.5 molar equivalents of azidobenzoic acid (ABA) with respect to GMA were dissolved in each of solution containing the copolymers, and the temperature of the solution was increased to 80° C. After that, 0.2 molar equivalent of triethylamine (TEA) with respect to GMA was added to the solution, and a reaction was performed for 48 hours to provide a copolymer containing a constitutional unit (GMA-Az) based on a GMA monomer containing an azidophenyl group.

<Synthesis of 4-(4-Azidobenzoyloxymethyl)styrene (AzSt) (Synthesis of Monomer from which Constitutional Unit (B) Represented by Formula (6) is Derived)>

6.42 g of azidobenzoic acid and 64 g of dimethylsulfoxide were weighed in a 200-milliliter recovery flask, and a temperature in the flask was increased to 50° C. to dissolve the materials. 2.72 g of potassium carbonate was added to the solution, and the mixture was stirred for 30 minutes. After a lapse of time, 5.46 g of chloromethylstyrene was added to the mixture, and a reaction was performed for 8 hours. After a lapse of 8 hours, 193.15 g of ethyl acetate was added to the resultant, and the organic layer was washed with 63.95 g of saturated saline five times, and was separated and extracted. The organic layer was dehydrated with sodium sulfate, and was then concentrated. The residue was dissolved in ethyl acetate so that the concentration of AzSt thus obtained became 50 mass %.

Various measurements in Polymerization Examples were performed in accordance with the following methods.

<Measurement of Weight-Average Molecular Weight>

5 mg of the resultant copolymer is dissolved in 1 g of a 0.1 mol/L aqueous solution of sodium sulfate, and its weight-average molecular weight is measured by gel permeation chromatography (GPC). Measurement conditions are as described below.

Apparatus: RI-8020, DP-8020, SD-8022, and AS-8020 (manufactured by Tosoh Corporation), and 865-CO (manufactured by JASCO Corporation), column: Shodex OHpak (manufactured by Showa Denko K.K.), mobile phase: a 0.1 mol/L aqueous solution of sodium sulfate, standard substance: pullulan, detection: a differential refractometer, calculation of weight-average molecular weight (Mw): a molecular weight calculation program (GPC program for SC-8020), flow rate: 1.0 mL/min, column temperature: 40° C., sample solution injection amount: 100 μL, measurement time: 30 minutes.

Polymerization Examples 1 to 8

Polymerization was performed in accordance with copolymer composition ratios and polymerization conditions (at 65° C. for 6 hours or at 60° C. for 6 hours) shown in Table 1, and purification by precipitation, ¹H-NMR analysis, and weight-average molecular weight measurement were performed. The results of the weight-average molecular weight measurement are shown in Table 1.

Polymerization Examples 9 to 16

Polymerization was performed in accordance with copolymer composition ratios and polymerization conditions (at 60° C. for 4 hours and then at 70° C. for 2 hours) shown in Tables 1 and 2, and ABA was added to GMA in each of the resultant copolymers (at 80° C. for 48 hours), followed by the performance of purification by precipitation, ¹H-NMR analysis, and weight-average molecular weight measurement. The results of the weight-average molecular weight measurement are shown in Tables 1 and 2.

Polymerization Examples 17 to 23

Polymerization was performed in accordance with copolymer composition ratios and polymerization conditions (at 60° C. for 4 hours and then at 70° C. for 2 hours) shown in Table 2, and purification by precipitation, ¹H-NMR analysis, and weight-average molecular weight measurement were performed. The results of the weight-average molecular weight measurement are shown in Table 2.

Comparative Polymerization Examples 1 to 4

Polymerization was performed in accordance with copolymer composition ratios and polymerization conditions shown in Table 2, followed by the performance of purification by precipitation, $^1$H-NMR analysis, and weight-average molecular weight measurement. The results of the weight-average molecular weight measurement are shown in Table 2.

Details about the materials used in the polymerization of the copolymers in Polymerization Examples and Comparative Polymerization Examples are described below (the materials are shown in abbreviations in tables).

MPC: 2-methacryloyloxyethyl phosphorylcholine
MBP: 4-methacryloyloxybenzophenone
MHP: 4-methacryloxy-2-hydroxybenzophenone
GMA: glycidyl methacrylate
BMA: butyl methacrylate
SMA: stearyl methacrylate
AzSt: 4-(4-azido-benzoyloxymethyl)styrene (50 mass % ethyl acetate solution product)
AEMA: aminoethyl methacrylate
ABA: azidobenzoic acid
TEA: triethylamine
EtOH: ethanol
nPA: n-propanol
PW: water (pure water)
AIBN: 2,2-azobisisobutyronitrile <Evaluation of Lubricity-Imparting Effect>

The copolymers (Polymerization Examples 1 to 23) in the lubricity-imparting agent of the present invention, and analogs thereof (Comparative Polymerization Examples 1 to 4) were evaluated for their lubricity-imparting effects.

A lubricity-imparting agent including each copolymer was dissolved in a solvent so that its concentration became a predetermined value. A plate made of polyethylene terephthalate was immersed in the solution for 30 seconds or more. Ethanol (EtOH) or a 50 wt % aqueous solution of ethanol (EtOH/PW) was used as the solvent. The plate was irradiated with light having a wavelength of 254 nm, and an unreacted lubricity-imparting agent was washed off with the solvent, followed by the measurement of the surface friction coefficient of the plate. Further, durability was evaluated from the result of the measurement of the surface friction coefficient. Conditions, such as the kinds of the copolymers, the contents of the copolymers, and the solvents, and the results of the evaluation are shown in Table 3 and Table 4 for the lubricity-imparting agents used in Examples and Comparative Examples. In addition, a similar evaluation was performed by using polyethylene terephthalate that had not been subjected to any surface treatment, and the obtained result was defined as Comparative Example 5.

<Surface Friction Coefficient>

The friction coefficient was measured with TRIBOGEAR (manufactured by Shinto Scientific Co., Ltd.) under the conditions of a sliding speed of 600 mm/min, a sliding distance of 50 mm, and a load of 10 g at room temperature in physiological saline while a contact terminal made of stainless steel was brought into contact with the plate.

<Durability>

The surface friction coefficient was measured by reciprocating the contact terminal five times at one and the same place, and a case in which the surface friction coefficient after the fifth reciprocation increased by 25% or more as compared to the friction coefficient after the first reciprocation was indicated by Symbol "+", and a case in which the increase was less than 25% was indicated by Symbol "++". In addition, a case in which the surface friction coefficient showed a value close to that of Comparative Example 5 at the time of the measurement on or before the fifth reciprocation was indicated by Symbol "×".

TABLE 1

|  |  |  | Polymerization Example 1 | Polymerization Example 2 | Polymerization Example 3 | Polymerization Example 4 | Polymerization Example 5 |
|---|---|---|---|---|---|---|---|
| Feed composition of polymerization of copolymer (g) | Monomer | MPC | 36.36 | 36.34 | 28.75 | 35.54 | 34.10 |
|  |  | MBP | 3.64 | — | 4.32 | 0.40 | 3.84 |
|  |  | MHP | — | 3.66 | — | — | — |
|  |  | GMA | — | — | — | — | — |
|  |  | BMA | — | — | 6.92 | 4.06 | 2.05 |
|  |  | SMA | — | — | — | — | — |
|  |  | AzSt | — | — | — | — | — |
|  |  | AEMA | — | — | — | — | — |
|  | Additive | ABA | — | — | — | — | — |
|  |  | TEA | — | — | — | — | — |
|  | Solvent | EtOH | 155.11 | 155.11 | 155.11 | 155.11 | 155.11 |
|  |  | nPA | — | — | — | — | — |
|  |  | PW | — | — | — | — | — |
|  | Initiator | AIBN | 4.89 | 4.89 | 4.89 | 4.89 | 4.89 |
|  | Total |  | 200.00 | 200.00 | 200.00 | 200.00 | 200.00 |
|  | Polymerization conditions (polymerization temperature and polymerization time) |  | At 65° C. for 6 hours | At 65° C. for 6 hours | At 65° C. for 6 hours | At 65° C. for 6 hours | At 60° C. for 6 hours |
| Composition ratio of copolymer (mol %) | Constitutional unit (A) | MPC | 90 | 90 | 60 | 80 | 80 |
|  | Constitutional unit (B) | MBP | 10 | — | 10 | 1 | 10 |
|  |  | MHP | — | 10 | — | — | — |
|  |  | GMA-Az | — | — | — | — | — |
|  |  | AzSt | — | — | — | — | — |
|  | Constitutional unit (C) | BMA | — | — | 30 | 19 | 10 |
|  |  | SMA | — | — | — | — | — |
|  | Others | AEMA | — | — | — | — | — |

TABLE 1-continued

|  |  |  | | | | | |
|---|---|---|---|---|---|---|---|
| Polymerization result | Water solubility | | YES | YES | YES | YES | YES |
|  | Weight-average molecular weight | | 132,000 | 106,000 | 118,000 | 145,000 | 520,000 |
|  | (Symbol of copolymer) | | P1 | P2 | P3 | P4 | P5 |

|  |  |  | Polymerization Example 6 | Polymerization Example 7 | Polymerization Example 8 | Polymerization Example 9 | Polymerization Example 10 |
|---|---|---|---|---|---|---|---|
| Feed composition of polymerization of copolymer (g) | Monomer | MPC | 32.78 | 28.57 | 31.84 | 39.81 | 39.01 |
|  |  | MBP | 7.02 | — | 3.59 | — | — |
|  |  | MHP | — | 4.55 | — | — | — |
|  |  | GMA | — | — | — | 0.19 | 0.99 |
|  |  | BMA | 0.20 | 6.88 | — | — | — |
|  |  | SMA | — | — | 4.57 | — | — |
|  |  | AzSt | — | — | — | — | — |
|  |  | AEMA | — | — | — | — | — |
|  | Additive | ABA | — | — | — | 0.33 | 1.70 |
|  |  | TEA | — | — | — | 0.03 | 0.14 |
|  | Solvent | EtOH | 155.11 | 155.11 | 155.11 | — | — |
|  |  | nPA | — | — | — | 154.14 | 154.14 |
|  |  | PW | — | — | — | — | — |
|  | Initiator | AIBN | 4.89 | 4.89 | 4.89 | 5.86 | 5.86 |
|  | Total | | 200.00 | 200.00 | 200.00 | 200.36 | 201.84 |
| Polymerization conditions (polymerization temperature and polymerization time) | | | At 65° C. for 6 hours | At 65° C. for 6 hours | At 65° C. for 6 hours | At 60° C. for 4 hours and then at 70° C. for 2 hours | At 60° C. for 4 hours and then at 70° C. for 2 hours |
| Composition ratio of copolymer (mol %) | Constitutional unit (A) | MPC | 80 | 60 | 80 | 99 | 95 |
|  | Constitutional unit (B) | MBP | 19 | — | 10 | — | — |
|  |  | MHP | — | 10 | — | — | — |
|  |  | GMA-Az | — | — | — | 1 | 5 |
|  |  | AzSt | — | — | — | — | — |
|  | Constitutional unit (C) | BMA | 1 | 30 | — | — | — |
|  |  | SMA | — | — | 10 | — | — |
|  | Others | AEMA | — | — | — | — | — |
| Polymerization result | Water solubility | | YES | YES | YES | YES | YES |
|  | Weight-average molecular weight | | 135,000 | 120,000 | 120,000 | 166,000 | 143,000 |
|  | (Symbol of copolymer) | | P6 | P7 | P8 | P9 | P10 |

|  |  |  | Polymerization Example 11 | Polymerization Example 12 | Polymerization Example 13 | Polymerization Example 14 |
|---|---|---|---|---|---|---|
| Feed composition of polymerization of copolymer (g) | Monomer | MPC | 35.70 | 30.28 | 35.70 | 35.70 |
|  |  | MBP | — | — | — | — |
|  |  | MHP | — | — | — | — |
|  |  | GMA | 4.30 | 2.43 | 4.08 | 2.15 |
|  |  | BMA | — | 7.29 | 0.21 | 2.15 |
|  |  | SMA | — | — | — | — |
|  |  | AzSt | — | — | — | — |
|  |  | AEMA | — | — | — | — |
|  | Additive | ABA | 7.39 | 4.18 | 7.02 | 3.70 |
|  |  | TEA | 0.61 | 0.35 | 0.58 | 0.31 |
|  | Solvent | EtOH | — | — | — | — |
|  |  | nPA | 154.14 | 154.14 | 154.14 | 154.14 |
|  |  | PW | — | — | — | — |
|  | Initiator | AIBN | 5.86 | 5.86 | 5.86 | 5.86 |
|  | Total | | 208.00 | 204.53 | 207.60 | 204.00 |

TABLE 1-continued

|  |  |  |  |  |  |  |
|---|---|---|---|---|---|---|
| | Polymerization conditions (polymerization temperature and polymerization time) | | | At 60° C. for 4 hours and then at 70° C. for 2 hours | At 60° C. for 4 hours and then at 70° C. for 2 hours | At 60° C. for 4 hours and then at 70° C. for 2 hours | At 60° C. for 4 hours and then at 70° C. for 2 hours |
| Composition ratio of copolymer (mol %) | Constitutional unit (A) | MPC | 80 | 60 | 80 | 80 |
| | Constitutional unit (B) | MBP | — | — | — | — |
| | | MHP | — | — | — | — |
| | | GMA-Az | 20 | 10 | 19 | 10 |
| | | AzSt | — | — | — | — |
| | Constitutional unit (C) | BMA | — | 30 | 1 | 10 |
| | | SMA | — | — | — | — |
| | Others | AEMA | — | — | — | — |
| Polymerization result | Water solubility | | YES | YES | YES | YES |
| | Weight-average molecular weight | | 125,000 | 58,000 | 98,000 | 85,000 |
| | (Symbol of copolymer) | | P11 | P12 | P13 | P14 |

TABLE 2

| | | | Polymerization Example 15 | Polymerization Example 16 | Polymerization Example 17 | Polymerization Example 18 | Polymerization Example 19 |
|---|---|---|---|---|---|---|---|
| Feed composition of polymerization of copolymer (g) | Monomer | MPC | 35.70 | 33.24 | 38.10 | 32.35 | 28.60 |
| | | MBP | — | — | — | — | — |
| | | MHP | — | — | — | — | — |
| | | GMA | 0.21 | 2.00 | — | — | — |
| | | BMA | 4.08 | — | — | — | 6.89 |
| | | SMA | — | 4.76 | — | — | — |
| | | AzSt | — | — | 3.79 | 15.30 | 9.02 |
| | | AEMA | — | — | — | — | — |
| | Additive | ABA | 0.37 | 3.45 | — | — | — |
| | | TEA | 0.03 | 0.29 | — | — | — |
| | Solvent | EtOH | — | — | — | — | — |
| | | nPA | 154.14 | 154.14 | 152.24 | 146.49 | 149.63 |
| | | PW | — | — | — | — | — |
| | Initiator | AIBN | 5.86 | 5.86 | 5.86 | 5.86 | 5.86 |
| | Total | | 200.40 | 203.74 | 200.00 | 200.00 | 200.00 |
| Polymerization conditions (polymerization temperature and polymerization time) | | | At 60° C. for 4 hours and then at 70° C. for 2 hours | At 60° C. for 4 hours and then at 70° C. for 2 hours | At 60° C. for 4 hours and then at 70° C. for 2 hours | At 60° C. for 4 hours and then at 70° C. for 2 hours | At 60° C. for 4 hours and then at 70° C. for 2 hours |
| Composition ratio of copolymer (mol %) | Constitutional unit (A) | MPC | 80 | 80 | 95 | 80 | 60 |
| | Constitutional unit (B) | MBP | — | — | — | — | — |
| | | MHP | — | — | — | — | — |
| | | GMA-Az | 1 | 10 | — | — | — |
| | | AzSt | — | — | 5 | 20 | 10 |
| | Constitutional unit (C) | BMA | 19 | — | — | — | 30 |
| | | SMA | — | 10 | — | — | — |
| | Others | AEMA | — | — | — | — | — |
| Polymerization result | Water solubility | | YES | YES | YES | YES | YES |
| | Weight-average molecular weight | | 66,000 | 55,000 | 72,000 | 63,000 | 25,000 |
| | (Symbol of (co)polymer) | | P15 | P16 | P17 | P18 | P19 |

TABLE 2-continued

| | | | Polymerization Example 20 | Polymerization Example 21 | Polymerization Example 22 | Polymerization Example 23 |
|---|---|---|---|---|---|---|
| Feed composition of polymerization of copolymer (g) | Monomer | MPC | 32.50 | 34.80 | 35.52 | 31.70 |
| | | MBP | — | — | — | — |
| | | MHP | — | — | — | — |
| | | GMA | — | — | — | — |
| | | BMA | 0.20 | 3.14 | 4.06 | — |
| | | SMA | — | — | — | 4.55 |
| | | AzSt | 14.60 | 4.11 | 0.84 | 7.50 |
| | | AEMA | — | — | — | — |
| | Additive | ABA | — | — | — | — |
| | | TEA | — | — | — | — |
| | Solvent | EtOH | — | — | — | — |
| | | nPA | 146.84 | 152.08 | 153.72 | 150.39 |
| | | PW | — | — | — | — |
| | Initiator | AIBN | 5.86 | 5.86 | 5.86 | 5.86 |
| | Total | | 200.00 | 200.00 | 200.00 | 200.00 |
| | Polymerization conditions (polymerization temperature and polymerization time) | | At 60° C. for 4 hours and then at 70° C. for 2 hours | At 60° C. for 4 hours and then at 70° C. for 2 hours | At 60° C. for 4 hours and then at 70° C. for 2 hours | At 60° C. for 4 hours and then at 70° C. for 2 hours |
| Composition ratio of copolymer (mol %) | Constitutional unit (A) | MPC | 80 | 80 | 80 | 80 |
| | Constitutional unit (B) | MBP | — | — | — | — |
| | | MHP | — | — | — | — |
| | | GMA-Az | — | — | — | — |
| | | AzSt | 19 | 5 | 1 | 10 |
| | Constitutional unit (C) | BMA | 1 | 15 | 19 | — |
| | | SMA | — | — | — | 10 |
| | Others | AEMA | — | — | — | — |
| Polymerization result | Water solubility | | YES | YES | YES | YES |
| | Weight-average molecular weight | | 50,000 | 49,000 | 33,000 | 28,000 |
| | (Symbol of (co)polymer) | | P20 | P21 | P22 | P23 |

| | | | Comparative Polymerization Example 1 | Comparative Polymerization Example 2 | Comparative Polymerization Example 3 | Comparative Polymerization Example 4 |
|---|---|---|---|---|---|---|
| Feed composition of polymerization of copolymer (g) | Monomer | MPC | 40.00 | 35.94 | 23.55 | 18.20 |
| | | MBP | — | — | — | — |
| | | MHP | — | — | — | — |
| | | GMA | — | — | — | — |
| | | BMA | — | 4.06 | 26.45 | — |
| | | SMA | — | — | — | — |
| | | AzSt | — | — | — | — |
| | | AEMA | — | — | — | 1.20 |
| | Additive | ABA | — | — | — | — |
| | | TEA | — | — | — | — |
| | Solvent | EtOH | 155.11 | 155.11 | 70.90 | — |
| | | nPA | — | — | — | — |
| | | PW | — | — | — | 80.00 |
| | Initiator | AIBN | 4.89 | 4.89 | 4.10 | 0.15 |
| | Total | | 200.00 | 200.00 | 125.00 | 99.65 |
| | Polymerization conditions (polymerization temperature and polymerization time) | | At 65° C. for 6 hours | At 65° C. for 6 hours | At 55° C. for 24 hours | At 60° C. for 8 hours |
| Composition ratio of copolymer (mol %) | Constitutional unit (A) | MPC | 100 | 81 | 30 | 90 |
| | Constitutional unit (B) | MBP | — | — | — | — |
| | | MHP | — | — | — | — |
| | | GMA-Az | — | — | — | — |
| | | AzSt | — | — | — | — |
| | Constitutional unit (C) | BMA | — | 19 | 70 | — |
| | | SMA | — | — | — | — |
| | Others | AEMA | — | — | — | 10 |

TABLE 2-continued

|  |  |  |  |  |  |
|---|---|---|---|---|---|
| Polymerization result | Water solubility | YES | YES | NO | YES |
|  | Weight-average molecular weight | 188,000 | 138,000 | 600,000 | 800,000 |
| (Symbol of (co)polymer) |  | Q1 | Q2 | Q3 | Q4 |

TABLE 3

|  |  | Example 1 | Example 2 | Example 3 | Example 4 | Example 5 | Example 6 | Example 7 |
|---|---|---|---|---|---|---|---|---|
| Kind of copolymer used |  | P1 | P2 | P3 | P4 | P5 | P6 | P7 |
| Ratio of copolymer used (%) |  | 100 | 100 | 100 | 100 | 100 | 100 | 100 |
| Other component: ratio of MPC (%) |  | — | — | — | — | — | — | — |
| Kind of solvent |  | EtOH | EtOH | EtOH | EtOH | EtOH | EtOH | EtOH |
| Friction coefficient | At concentration of 1.0 mass % | 0.101 | 0.071 | 0.081 | 0.087 | 0.054 | 0.075 | 0.062 |
|  | At concentration of 0.5 mass % | 0.098 | 0.092 | 0.079 | 0.074 | 0.062 | 0.074 | 0.069 |
|  | At concentration of 0.1 mass % | 0.095 | 0.103 | 0.095 | 0.091 | 0.061 | 0.082 | 0.085 |
| Durability | At concentration of 1.0 mass % | ++ | ++ | ++ | + | ++ | ++ | ++ |
|  | At concentration of 0.5 mass % | ++ | ++ | ++ | + | ++ | ++ | ++ |
|  | At concentration of 0.1 mass % | + | + | + | + | + | + | + |

|  |  | Example 8 | Example 9 | Example 10 | Example 11 | Example 12 | Example 13 | Example 14 |
|---|---|---|---|---|---|---|---|---|
| Kind of copolymer used |  | P8 | P9 | P10 | P11 | P12 | P13 | P14 |
| Ratio of copolymer used (%) |  | 100 | 100 | 100 | 100 | 100 | 100 | 100 |
| Other component: ratio of MPC (%) |  | — | — | — | — | — | — | — |
| Kind of solvent |  | EtOH | EtOH | EtOH | EtOH | EtOH | EtOH | EtOH |
| Friction coefficient | At concentration of 1.0 mass % | 0.025 | 0.019 | 0.017 | 0.017 | 0.018 | 0.014 | 0.009 |
|  | At concentration of 0.5 mass % | 0.031 | 0.017 | 0.014 | 0.014 | 0.014 | 0.017 | 0.012 |
|  | At concentration of 0.1 mass % | 0.03 | 0.028 | 0.025 | 0.021 | 0.029 | 0.02 | 0.018 |
| Durability | At concentration of 1.0 mass % | ++ | ++ | ++ | ++ | ++ | ++ | ++ |
|  | At concentration of 0.5 mass % | ++ | ++ | ++ | ++ | ++ | ++ | ++ |
|  | At concentration of 0.1 mass % | + | + | + | + | ++ | + | + |

TABLE 4

|  |  | Example 15 | Example 16 | Example 17 | Example 18 | Example 19 | Example 20 | Example 21 | Example 22 | Example 23 |
|---|---|---|---|---|---|---|---|---|---|---|
| Kind of copolymer used |  | P15 | P16 | P17 | P18 | P19 | P20 | P21 | P22 | P23 |
| Ratio of copolymer used (%) |  | 100 | 100 | 100 | 100 | 100 | 100 | 100 | 100 | 100 |
| Other component: ratio of MPC (%) |  | — | — | — | — | — | — | — | — | — |
| Kind of solvent |  | EtOH | EtOH | EtOH | EtOH | EtOH | EtOH | EtOH | EtOH | EtOH |
| Friction coefficient | At concentration of 1.0 mass % | 0.01 | 0.008 | 0.018 | 0.021 | 0.012 | 0.007 | 0.009 | 0.014 | 0.017 |

TABLE 4-continued

|  |  |  |  |  |  |  |  |  |  |
|---|---|---|---|---|---|---|---|---|---|
|  | At concentration of 0.5 mass % | 0.008 | 0.012 | 0.015 | 0.023 | 0.009 | 0.012 | 0.012 | 0.011 | 0.011 |
|  | At concentration of 0.1 mass % | 0.018 | 0.031 | 0.027 | 0.04 | 0.011 | 0.011 | 0.015 | 0.021 | 0.019 |
| Durability | At concentration of 1.0 mass % | ++ | ++ | ++ | ++ | ++ | ++ | ++ | ++ | ++ |
|  | At concentration of 0.5 mass % | ++ | ++ | ++ | ++ | ++ | ++ | ++ | ++ | ++ |
|  | At concentration of 0.1 mass % | + | ++ | + | + | ++ | + | ++ | + | ++ |

|  |  | Example 24 | Example 25 | Example 26 | Comparative Example 1 | Comparative Example 2 | Comparative Example 3 | Comparative Example 4 | Comparative Example 5 |
|---|---|---|---|---|---|---|---|---|---|
|  | Kind of copolymer used | P2 | P12 | P20 | Q1 | Q2 | Q3 | Q4 | — |
|  | Ratio of copolymer used (%) | 50 | 50 | 50 | 100 | 100 | 100 | 100 | — |
|  | Other component: ratio of MPC (%) | 50 | 50 | 50 | — | — | — | — | — |
|  | Kind of solvent | EtOH/PW | EtOH/PW | EtOH/PW | EtOH | EtOH | EtOH | EtOH | EtOH |
| Friction coefficient | At concentration of 1.0 mass % | – | – | – | 0.189 | 0.201 | 0.072 | 0.194 | 0.194 (free of copolymer) |
|  | At concentration of 0.5 mass % | 0.008 | 0.006 | 0.005 | – | – | – | – |  |
|  | At concentration of 0.1 mass % | 0.006 | – | – | – | – | – | – |  |
| Durability | At concentration of 1.0 mass % | – | – | – | x | x | x | x | x |
|  | At concentration of 0.5 mass % | ++ | ++ | ++ | – | – | – | – | – |
|  | At concentration of 0.1 mass % | ++ | – | – | – | – | – | – | – |

As is apparent from the results of Table 3 and Table 4, the friction coefficient of a substrate surface was able to be reduced by: coating the substrate surface with a lubricity-imparting agent including a copolymer containing a constitutional unit based on 2-methacryloyloxyethyl phosphorylcholine and a constitutional unit based on a photoreactive functional group-containing monomer, or a copolymer containing a constitutional unit based on 2-methacryloyloxyethyl phosphorylcholine, a constitutional unit based on a photoreactive functional group-containing monomer, and a constitutional unit based on a hydrophobic group-containing monomer; and irradiating the substrate surface with light. In addition, the friction coefficient maintained a low friction coefficient even after the 5-reciprocation measurement.

Meanwhile, as can be seen from the results of Table 4, in each of Comparative Example 1 (in which the substrate surface was coated with the polymer formed only of the constitutional unit based on 2-methacryloyloxyethyl phosphorylcholine), Comparative Example 2 (in which the substrate surface was coated with the water-soluble copolymer that had only the constitutional unit based on 2-methacryloyloxyethyl phosphorylcholine and the constitutional unit based on a hydrophobic group-containing monomer, and was free of any constitutional unit based on a photoreactive functional group-containing monomer), and Comparative Example 4 (in which the substrate surface was coated with the copolymer that was free of any constitutional unit based on a hydrophobic group-containing monomer and any constitutional unit based on a photoreactive functional group-containing monomer, but had the constitutional unit based on 2-methacryloyloxyethyl phosphorylcholine and the constitutional unit having an amino group), no reduction in friction coefficient was observed because no copolymer layer was formed on the substrate surface by the photoirradiation, and hence the value of the friction coefficient was comparable to that of Comparative Example 5 (polyethylene terephthalate that had not been subjected to any surface treatment). In addition, it was revealed that in Comparative Example 3 (in which the substrate surface was coated with the water-insoluble copolymer that had only the constitutional unit based on 2-methacryloyloxyethyl phosphorylcholine and the constitutional unit based on a hydrophobic group-containing monomer, and was free of any constitutional unit based on a photoreactive functional group-containing monomer), the friction coefficient in the first measurement was able to be reduced because the copolymer was water-insoluble, but as the measurement was repeated, the value of the friction coefficient increased, in other words, the friction coefficient was deficient in durability.

It was confirmed from the foregoing results that the lubricity-imparting agent of the present invention was able to impart durable lubricity to a substrate surface through the coating of the substrate surface with the agent and the irradiation of the substrate surface with light.

INDUSTRIAL APPLICABILITY

The lubricity-imparting agent of the present invention can impart durable lubricity to a substrate surface. In addition, the article of the present invention has highly durable lubricity.

The invention claimed is:

1. A method of imparting lubricity to a substrate surface, comprising the following steps (1) and (2):
   (1) a step of coating the substrate surface with a copolymer having a weight-average molecular weight of from 10,000 to 1,000,000, and
   (2) a step of irradiating the substrate surface coated in the step (1) with light to form a crosslinked body on the substrate surface,
   wherein the copolymer contains 60 mol % to 99 mol % of a 2-methacryloyloxyethyl phosphorylcholine constitutional unit (A) represented by the following formula (1) and 1 mol % to 40 mol % of a photoreactive functional group-containing constitutional unit (B) represented by any one of the following formulae (2), (3), and (6):

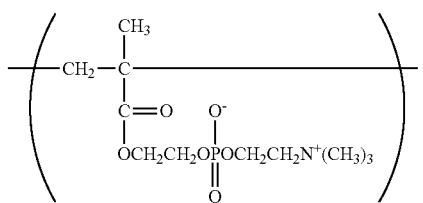
(1)

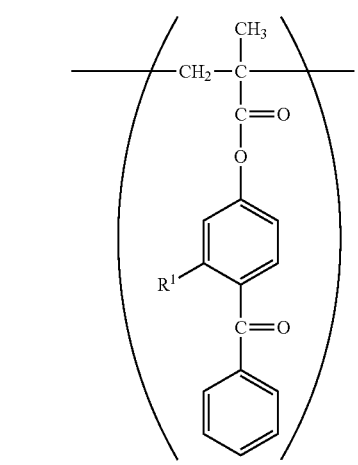
(2)

in the formula (2), $R^1$ represents a hydrogen atom or a hydroxyl group;

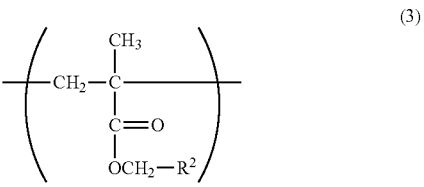
(3)

in the formula (3), $R^2$ represents the following formula (4) or the following formula (5);

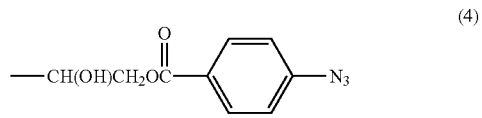
(4)

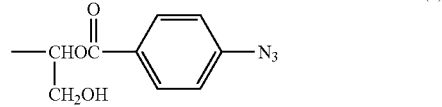
(5)

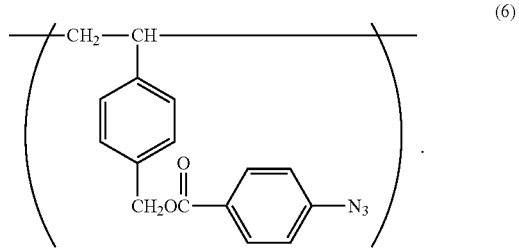
(6)

2. The method according to claim 1, wherein the constitutional unit (B) comprises 4-methacryloyloxybenzophenone.

3. The method according to claim 1, wherein the constitutional unit (B) comprises 4 methacryloxy-2-hydroxybenzophenone.

4. The method according to claim 1, wherein the constitutional unit (B) is represented by formula (3) which is a copolymer containing glycidyl methacrylate.

5. The method according to claim 1, wherein the constitutional unit (B) comprises 4 (4 azidobenzoyloxymethyl) styrene.

6. A method of imparting lubricity to a substrate surface, comprising the following steps (1) and (2):
   (1) a step of coating the substrate surface with a copolymer having a weight-average molecular weight of from 10,000 to 1,000,000, and
   (2) a step of irradiating the substrate surface coated in the step (1) with light to form a crosslinked body on the substrate surface,
   wherein the copolymer contains 60 mol % to 98 mol % of a 2-methacryloyloxyethyl phosphorylcholine constitutional unit (A) represented by the following formula (1), 1 mol % to 39 mol % of a photoreactive functional group-containing constitutional unit (B) represented by any one of the following formulae (2), (3), and (6), and 1 mol % to 30 mol % of a hydrophobic group-containing constitutional unit (C) represented by the following formula (7):

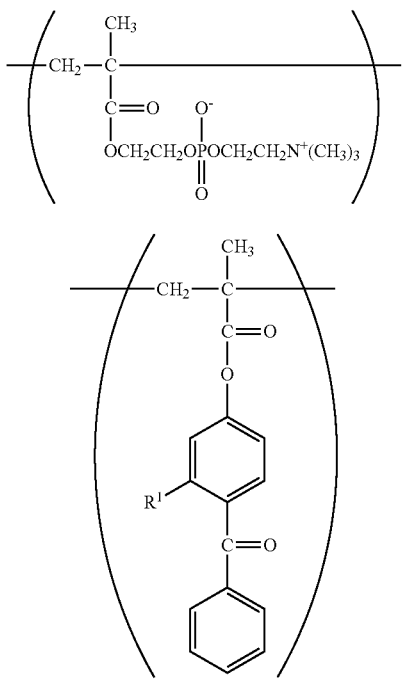
(1)

(2)

in the formula (2), R¹ represents a hydrogen atom or a hydroxyl group;

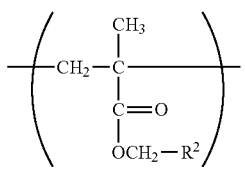
(3)

in the formula (3), R² represents the following formula (4) or the following formula (5):

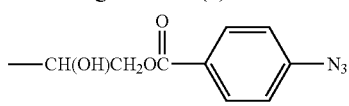
(4)

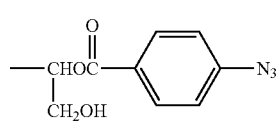
(5)

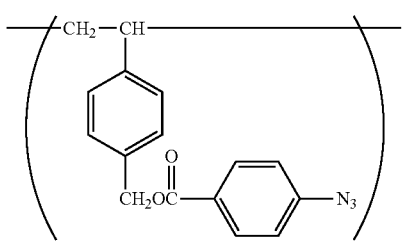
(6)

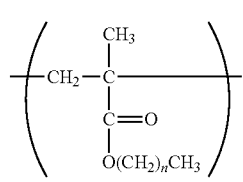
(7)

in the formula (7), n represents an integer from 3 to 17.

7. The method according to claim 6, wherein the constitutional unit (B) comprises 4 methacryloyloxybenzophenone, and the constitutional unit (C) comprises butyl methacrylate.

8. The method according to claim 6, wherein the constitutional unit (B) comprises 4 methacryloxy-2-hydroxybenzophenone, and the constitutional unit (C) comprises butyl methacrylate.

9. The method according to claim 6, wherein the constitutional unit (B) is represented by formula (3) which is a copolymer containing glycidyl methacrylate, and the constitutional unit (C) comprises butyl methacrylate.

10. The method according to claim 6, wherein the constitutional unit (B) comprises 4 (4 azidobenzoyloxymethyl) styrene, and the constitutional unit (C) comprises butyl methacrylate.

11. A crosslinked body, which is obtained by irradiating a copolymer having a weight-average molecular weight of from 10,000 to 1,000,000, the copolymer containing 60 mol % to 99 mol % of a 2-methacryloyloxyethyl phosphorylcholine constitutional unit (A) represented by the following formula (1) and 1 mol % to 40 mol % of a photoreactive functional group-containing constitutional unit (B) represented by any one of the following formulae (2), (3), and (6):

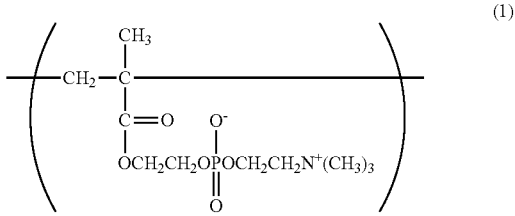
(1)

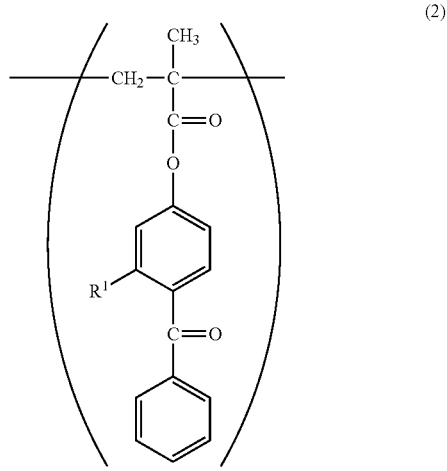
(2)

in the formula (2), R¹ represents a hydrogen atom or a hydroxyl group;

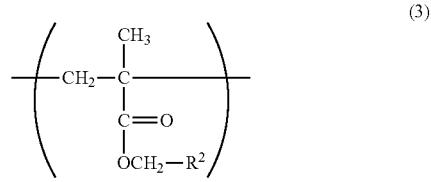
(3)

in the formula (3), R² represents the following formula (4) or the following formula (5):

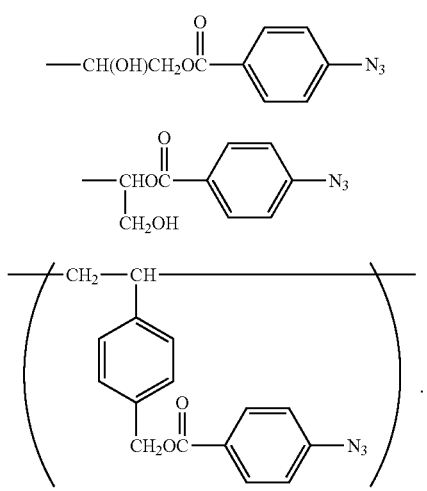

12. A crosslinked body, which is obtained by irradiating a copolymer having a weight-average molecular weight of from 10,000 to 1,000,000, the copolymer containing 60 mol % to 98 mol % of a 2-methacryloyloxyethyl phosphorylcholine constitutional unit (A) represented by the following formula (1), 1 mol % to 39 mol % of a photoreactive functional group-containing constitutional unit (B) represented by any one of the following formulae (2), (3), and (6), and 1 mol % to 30 mol % of a hydrophobic group-containing constitutional unit (C) represented by the following formula (7):

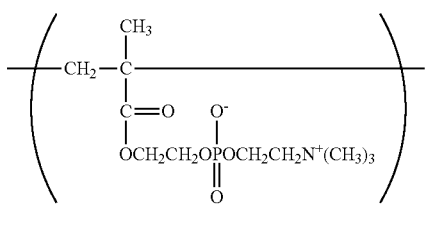

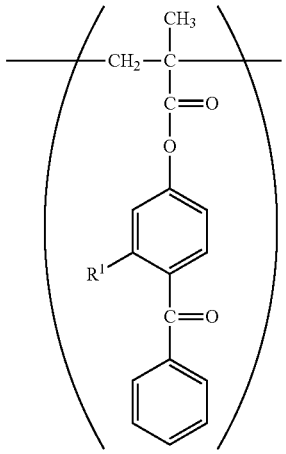

in the formula (2), $R^1$ represents a hydrogen atom or a hydroxyl group;

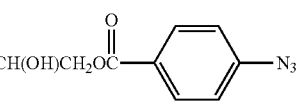

in the formula (3), $R^2$ represents the following formula (4) or the following formula (5);

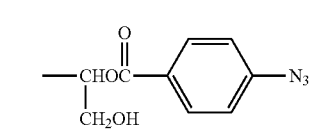

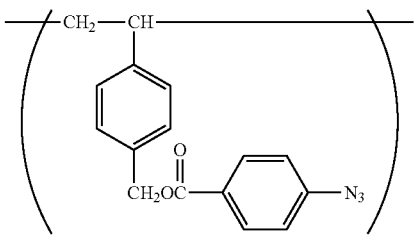

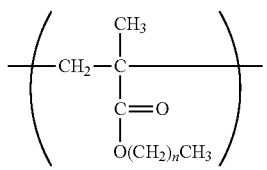

in the formula (7), n represents an integer from 3 to 17.

13. An article, comprising the crosslinked body of claim 11.

14. An article, comprising the crosslinked body of claim 12.

* * * * *